(12) United States Patent
Scheiner et al.

(10) Patent No.: US 8,126,560 B2
(45) Date of Patent: *Feb. 28, 2012

(54) STIMULATION LEAD FOR STIMULATING THE BARORECEPTORS IN THE PULMONARY ARTERY

(75) Inventors: Avram Scheiner, Vadnais Heights, MN (US); Ronald W. Heil, Jr., Roseville, MN (US); Peter T. Kelley, Buffalo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1862 days.

This patent is subject to a terminal disclaimer.

(21) Appl. No.: 10/746,852

(22) Filed: Dec. 24, 2003

(65) Prior Publication Data

US 2005/0149155 A1    Jul. 7, 2005

(51) Int. Cl.
*A61N 1/18* (2006.01)
*A61N 1/362* (2006.01)

(52) U.S. Cl. ............ 607/44; 607/42; 607/9

(58) Field of Classification Search ........ 607/125, 607/9, 42, 44
See application file for complete search history.

(56) References Cited

U.S. PATENT DOCUMENTS

| | | |
|---|---|---|
| 3,421,511 A | 1/1969 | Schwartz et al. |
| 3,522,811 A | 8/1970 | Seymour et al. |
| 3,650,277 A | 3/1972 | Sjostrand et al. |
| 4,357,946 A | 11/1982 | Dutcher et al. |
| 4,397,946 A | 8/1983 | Imada et al. |
| 4,730,619 A | 3/1988 | Koning et al. |
| 4,770,177 A | 9/1988 | Schroeppel |
| 4,791,931 A | 12/1988 | Slate .................. 128/419 |
| 4,936,304 A | 6/1990 | Kresh et al. |
| 4,960,129 A | 10/1990 | dePaola et al. |
| 5,024,222 A | 6/1991 | Thacker |
| 5,052,388 A | 10/1991 | Sivula et al. |
| 5,111,815 A | 5/1992 | Mower .................. 128/419 |
| 5,190,035 A | 3/1993 | Salo et al. .............. 128/419 |
| 5,199,428 A | 4/1993 | Obel et al. ............ 128/419 C |
| 5,203,326 A | 4/1993 | Collins .............. 128/419 PG |
| 5,243,980 A | 9/1993 | Mehra .......................... 607/6 |

(Continued)

FOREIGN PATENT DOCUMENTS

EP    0547734 A2    6/1993

(Continued)

OTHER PUBLICATIONS

Abraham, W T., "Miracle Study Group. Multicenter InSync Randomized Clinical Evaluation. Cardiac resynchronization in chronic heart failure", *New England Journal of Medicine*, 346(24), (Jul. 13, 2002),1845-53.

(Continued)

*Primary Examiner* — Carl H. Layno
*Assistant Examiner* — Jon-Eric C. Morales
(74) *Attorney, Agent, or Firm* — Schwegman, Lundberg & Woessner, P.A.

(57) ABSTRACT

An apparatus includes a flexible lead body extending from a proximal end to a distal end, the distal end having a biased portion having an outer diameter dimensioned to abut a wall of a pulmonary artery, an electrode coupled proximate the distal end, and an implantable pulse generator electrically coupled to the electrode. The implantable pulse generator is adapted to deliver a baroreflex stimulation signal to a baroreceptor in the pulmonary artery via the electrode.

34 Claims, 4 Drawing Sheets

U.S. PATENT DOCUMENTS

| | | | | |
|---|---|---|---|---|
| 5,318,592 | A | 6/1994 | Schaldach | 607/5 |
| 5,324,316 | A | 6/1994 | Schulman et al. | |
| 5,330,507 | A | 7/1994 | Schwartz | 607/14 |
| 5,334,221 | A | 8/1994 | Bardy | |
| 5,356,425 | A | 10/1994 | Bardy et al. | 607/14 |
| 5,374,282 | A | 12/1994 | Nichols et al. | |
| 5,403,351 | A | 4/1995 | Saksena | |
| 5,409,009 | A | 4/1995 | Olson | |
| 5,411,531 | A | 5/1995 | Hill et al. | 607/14 |
| 5,437,285 | A | 8/1995 | Verrier et al. | 128/702 |
| 5,507,784 | A | 4/1996 | Hill et al. | 607/14 |
| 5,513,644 | A | 5/1996 | McClure et al. | |
| 5,522,854 | A | 6/1996 | Ideker et al. | 607/6 |
| 5,540,730 | A | 7/1996 | Terry, Jr. et al. | |
| 5,562,711 | A | 10/1996 | Yerich et al. | |
| 5,578,061 | A | 11/1996 | Stroetmann et al. | 607/4 |
| 5,593,430 | A | 1/1997 | Renger | |
| 5,651,378 | A | 7/1997 | Matheny et al. | |
| 5,658,318 | A | 8/1997 | Stroetmann et al. | 607/6 |
| 5,662,689 | A | 9/1997 | Elsberry et al. | |
| 5,690,681 | A | 11/1997 | Geddes et al. | 607/2 |
| 5,700,282 | A | 12/1997 | Zabara | 607/9 |
| 5,707,400 | A | 1/1998 | Terry, Jr. et al. | |
| 5,749,900 | A | 5/1998 | Schroeppel et al. | |
| 5,792,187 | A | 8/1998 | Adams | |
| 5,817,131 | A | 10/1998 | Elsberry et al. | |
| 5,902,324 | A | 5/1999 | Thompson et al. | |
| 5,913,876 | A | 6/1999 | Taylor et al. | |
| 5,916,239 | A | 6/1999 | Geddes et al. | |
| 6,006,122 | A * | 12/1999 | Smits | 600/373 |
| 6,006,134 | A | 12/1999 | Hill et al. | 607/9 |
| 6,035,233 | A | 3/2000 | Schroeppel et al. | |
| 6,058,331 | A | 5/2000 | King | 607/62 |
| 6,073,048 | A | 6/2000 | Kieval et al. | 607/17 |
| 6,076,014 | A | 6/2000 | Alt | |
| 6,104,956 | A | 8/2000 | Naritoku et al. | |
| 6,134,470 | A | 10/2000 | Hartlaub | 607/14 |
| 6,141,590 | A | 10/2000 | Renirie et al. | |
| 6,144,878 | A | 11/2000 | Schroeppel et al. | |
| 6,161,042 | A | 12/2000 | Hartley et al. | 607/20 |
| 6,161,048 | A | 12/2000 | Sluijter et al. | |
| 6,164,284 | A | 12/2000 | Schulman et al. | |
| 6,169,918 | B1 | 1/2001 | Haefner et al. | |
| 6,178,349 | B1 | 1/2001 | Kieval | 607/118 |
| 6,181,966 | B1 | 1/2001 | Nigam | 607/4 |
| 6,240,314 | B1 | 5/2001 | Plicchi et al. | 607/14 |
| 6,240,316 | B1 | 5/2001 | Richmond et al. | |
| 6,266,564 | B1 | 7/2001 | Hill et al. | |
| 6,272,377 | B1 | 8/2001 | Sweeney et al. | 600/515 |
| 6,285,907 | B1 | 9/2001 | Kramer et al. | |
| 6,292,695 | B1 | 9/2001 | Webster, Jr. et al. | 607/14 |
| 6,292,703 | B1 | 9/2001 | Meier et al. | |
| 6,308,104 | B1 | 10/2001 | Taylor et al. | |
| 6,341,236 | B1 | 1/2002 | Osorio et al. | |
| 6,349,233 | B1 | 2/2002 | Adams | |
| 6,371,922 | B1 | 4/2002 | Baumann et al. | 600/485 |
| 6,381,499 | B1 | 4/2002 | Taylor et al. | |
| 6,400,982 | B2 | 6/2002 | Sweeney et al. | 600/515 |
| 6,405,079 | B1 | 6/2002 | Ansarinia | |
| 6,411,845 | B1 | 6/2002 | Mower | |
| 6,421,557 | B1 | 7/2002 | Meyer | 600/516 |
| 6,438,423 | B1 | 8/2002 | Rezai et al. | |
| 6,442,424 | B1 | 8/2002 | Ben-Haim et al. | |
| 6,447,443 | B1 | 9/2002 | Keogh et al. | |
| 6,449,507 | B1 | 9/2002 | Hill et al. | 607/9 |
| 6,473,644 | B1 | 10/2002 | Terry, Jr. et al. | 607/2 |
| 6,477,418 | B2 | 11/2002 | Plicchi et al. | |
| 6,487,442 | B1 | 11/2002 | Wood | |
| 6,487,446 | B1 | 11/2002 | Hill et al. | |
| 6,487,450 | B1 | 11/2002 | Chen | 607/9 |
| 6,493,585 | B2 | 12/2002 | Plicchi et al. | 607/14 |
| 6,511,500 | B1 | 1/2003 | Rahme | 607/1 |
| 6,522,926 | B1 | 2/2003 | Kieval et al. | 607/44 |
| 6,532,388 | B1 | 3/2003 | Hill et al. | 607/2 |
| 6,542,774 | B2 | 4/2003 | Hill et al. | 607/9 |
| 6,564,096 | B2 | 5/2003 | Mest | 607/14 |
| 6,571,121 | B2 | 5/2003 | Schroeppel et al. | |
| 6,571,122 | B2 | 5/2003 | Schroeppel et al. | |
| 6,574,512 | B1 * | 6/2003 | Zhang et al. | 607/122 |
| 6,584,362 | B1 * | 6/2003 | Scheiner et al. | 607/122 |
| 6,600,954 | B2 | 7/2003 | Cohen et al. | |
| 6,610,713 | B2 | 8/2003 | Tracey | |
| 6,611,713 | B2 | 8/2003 | Schauerte | 607/14 |
| 6,622,041 | B2 | 9/2003 | Terry, Jr. et al. | 607/9 |
| 6,628,987 | B1 | 9/2003 | Hill et al. | 607/9 |
| 6,662,052 | B1 | 12/2003 | Sarwal et al. | |
| 6,668,191 | B1 | 12/2003 | Boveja | |
| 6,684,105 | B2 | 1/2004 | Cohen et al. | |
| 6,690,971 | B2 | 2/2004 | Schauerte et al. | |
| 6,718,203 | B2 | 4/2004 | Weiner et al. | |
| 6,718,207 | B2 | 4/2004 | Connelly | |
| 6,718,208 | B2 | 4/2004 | Hill et al. | |
| 6,735,471 | B2 | 5/2004 | Hill et al. | |
| 6,763,268 | B2 | 7/2004 | MacDonald et al. | |
| 6,778,854 | B2 | 8/2004 | Puskas | |
| 6,788,970 | B1 | 9/2004 | Park et al. | |
| 6,799,069 | B2 | 9/2004 | Weiner et al. | |
| 6,804,561 | B2 | 10/2004 | Stover | |
| RE38,654 | E | 11/2004 | Hill et al. | |
| 6,838,471 | B2 | 1/2005 | Tracey | |
| 6,839,592 | B2 | 1/2005 | Grandjean | |
| 6,845,267 | B2 | 1/2005 | Harrison et al. | |
| RE38,705 | E | 2/2005 | Hill et al. | |
| 6,882,886 | B1 * | 4/2005 | Witte et al. | 607/122 |
| 6,885,888 | B2 | 4/2005 | Rezai | |
| 6,904,318 | B2 | 6/2005 | Hill et al. | |
| 6,912,419 | B2 | 6/2005 | Hill et al. | |
| 6,922,585 | B2 | 7/2005 | Zhou et al. | |
| 6,928,320 | B2 | 8/2005 | King | |
| 6,928,326 | B1 | 8/2005 | Levine | |
| 6,934,583 | B2 | 8/2005 | Weinberg et al. | |
| 6,937,896 | B1 | 8/2005 | Kroll | |
| 6,942,622 | B1 | 9/2005 | Turcott | |
| 6,985,774 | B2 | 1/2006 | Kieval et al. | |
| 7,025,730 | B2 | 4/2006 | Cho et al. | |
| 7,058,450 | B2 | 6/2006 | Struble et al. | |
| 7,092,755 | B2 | 8/2006 | Florio | |
| 7,136,704 | B2 | 11/2006 | Schulman | |
| 7,139,607 | B1 | 11/2006 | Shelchuk | |
| 7,155,284 | B1 | 12/2006 | Whitehurst et al. | |
| 7,158,832 | B2 | 1/2007 | Kieval et al. | |
| 7,167,756 | B1 | 1/2007 | Torgerson et al. | |
| 7,194,313 | B2 | 3/2007 | Libbus | |
| 7,218,964 | B2 | 5/2007 | Hill et al. | |
| 7,245,967 | B1 | 7/2007 | Shelchuk | |
| 7,260,431 | B2 | 8/2007 | Libbus et al. | |
| 7,277,761 | B2 | 10/2007 | Shelchuk | |
| 7,294,334 | B1 | 11/2007 | Michal et al. | |
| 7,299,086 | B2 | 11/2007 | McCabe et al. | |
| 7,321,793 | B2 | 1/2008 | Ben Ezra et al. | |
| 7,333,854 | B1 | 2/2008 | Brewer et al. | |
| 7,403,819 | B1 | 7/2008 | Shelchuk et al. | |
| 7,460,906 | B2 | 12/2008 | Libbus | |
| 7,480,532 | B2 | 1/2009 | Kieval et al. | |
| 7,486,991 | B2 | 2/2009 | Libbus et al. | |
| 7,493,161 | B2 | 2/2009 | Libbus et al. | |
| 7,499,748 | B2 | 3/2009 | Moffitt et al. | |
| 7,509,166 | B2 | 3/2009 | Libbus | |
| 7,542,800 | B2 | 6/2009 | Libbus et al. | |
| 7,548,780 | B2 | 6/2009 | Libbus et al. | |
| 7,551,958 | B2 | 6/2009 | Libbus et al. | |
| 7,555,341 | B2 | 6/2009 | Moffitt et al. | |
| 7,561,923 | B2 | 7/2009 | Libbus et al. | |
| 7,570,999 | B2 | 8/2009 | Libbus et al. | |
| 7,572,228 | B2 | 8/2009 | Wolinsky et al. | |
| 7,584,004 | B2 | 9/2009 | Caparso et al. | |
| 7,587,238 | B2 | 9/2009 | Moffitt et al. | |
| 7,617,003 | B2 * | 11/2009 | Caparso et al. | 607/116 |
| 7,643,875 | B2 | 1/2010 | Heil, Jr. et al. | |
| 7,647,114 | B2 | 1/2010 | Libbus | |
| 7,657,312 | B2 | 2/2010 | Pastore et al. | |
| 7,706,884 | B2 | 4/2010 | Libbus | |
| 7,734,348 | B2 | 6/2010 | Zhang et al. | |
| 7,765,000 | B2 | 7/2010 | Zhang et al. | |
| 7,769,450 | B2 | 8/2010 | Libbus et al. | |
| 7,783,353 | B2 | 8/2010 | Libbus et al. | |
| 7,869,881 | B2 | 1/2011 | Libbus et al. | |

| | | |
|---|---|---|
| 8,000,793 B2 | 8/2011 | Libbus |
| 8,024,050 B2 | 9/2011 | Libbus et al. |
| 2001/0020136 A1 | 9/2001 | Sweeney et al. |
| 2002/0004670 A1 | 1/2002 | Florio et al. |
| 2002/0010493 A1 | 1/2002 | Poezevara et al. |
| 2002/0016344 A1 | 2/2002 | Tracey |
| 2002/0016550 A1 | 2/2002 | Sweeney et al. |
| 2002/0026221 A1 | 2/2002 | Hill et al. ................... 607/9 |
| 2002/0026222 A1 | 2/2002 | Schauerte et al. ........... 607/14 |
| 2002/0026228 A1* | 2/2002 | Schauerte ................. 607/122 |
| 2002/0032468 A1 | 3/2002 | Hill et al. |
| 2002/0042637 A1 | 4/2002 | Stover |
| 2002/0058877 A1 | 5/2002 | Baumann et al. ............ 600/485 |
| 2002/0068875 A1 | 6/2002 | Schroeppel et al. |
| 2002/0072776 A1 | 6/2002 | Osorio et al. |
| 2002/0077670 A1 | 6/2002 | Archer et al. |
| 2002/0082661 A1 | 6/2002 | Plicchi et al. |
| 2002/0091415 A1 | 7/2002 | Lovett et al. |
| 2002/0095139 A1 | 7/2002 | Keogh et al. |
| 2002/0107553 A1 | 8/2002 | Hill et al. ................... 607/18 |
| 2002/0107557 A1 | 8/2002 | Edell et al. |
| 2002/0116030 A1 | 8/2002 | Rezai |
| 2002/0120304 A1 | 8/2002 | Mest ........................... 607/14 |
| 2002/0123769 A1 | 9/2002 | Panken et al. |
| 2002/0138109 A1 | 9/2002 | Keogh et al. |
| 2002/0143369 A1 | 10/2002 | Hill et al. ................... 607/9 |
| 2002/0161410 A1 | 10/2002 | Kramer et al. |
| 2002/0165586 A1 | 11/2002 | Hill et al. ................... 607/9 |
| 2002/0183237 A1 | 12/2002 | Puskas |
| 2002/0183793 A1 | 12/2002 | Struble et al. |
| 2002/0188325 A1 | 12/2002 | Hill et al. |
| 2002/0188326 A1 | 12/2002 | Zheng et al. |
| 2002/0193843 A1 | 12/2002 | Hill et al. |
| 2002/0198570 A1 | 12/2002 | Puskas |
| 2002/0198571 A1 | 12/2002 | Puskas |
| 2003/0003052 A1 | 1/2003 | Hampton ...................... 424/9.2 |
| 2003/0004549 A1 | 1/2003 | Hill et al. ................... 607/9 |
| 2003/0018368 A1 | 1/2003 | Ansarinia |
| 2003/0023279 A1 | 1/2003 | Spinelli et al. |
| 2003/0036773 A1 | 2/2003 | Whitehurst et al. |
| 2003/0040774 A1 | 2/2003 | Terry et al. |
| 2003/0045909 A1 | 3/2003 | Gross et al. ................. 607/9 |
| 2003/0045914 A1 | 3/2003 | Cohen et al. |
| 2003/0060848 A1 | 3/2003 | Keival et al. ................ 607/2 |
| 2003/0060857 A1 | 3/2003 | Perrson et al. ............... 607/44 |
| 2003/0060858 A1 | 3/2003 | Kieval et al. ................ 607/44 |
| 2003/0074039 A1 | 4/2003 | Puskas |
| 2003/0078623 A1 | 4/2003 | Weinberg et al. |
| 2003/0078629 A1 | 4/2003 | Chen .......................... 607/9 |
| 2003/0100924 A1 | 5/2003 | Foreman et al. ............. 607/9 |
| 2003/0105493 A1 | 6/2003 | Salo |
| 2003/0114905 A1 | 6/2003 | Kuzma |
| 2003/0125770 A1 | 7/2003 | Fuimaono et al. |
| 2003/0149450 A1 | 8/2003 | Mayberg ..................... 607/3 |
| 2003/0158584 A1 | 8/2003 | Cates et al. |
| 2003/0176818 A1 | 9/2003 | Schuler et al. |
| 2003/0181951 A1 | 9/2003 | Cates |
| 2003/0191403 A1 | 10/2003 | Zhou et al. |
| 2003/0191404 A1 | 10/2003 | Klein |
| 2003/0195578 A1 | 10/2003 | Perron et al. |
| 2003/0212440 A1 | 11/2003 | Boveja ...................... 607/46 |
| 2003/0212445 A1 | 11/2003 | Weinberg |
| 2003/0216790 A1 | 11/2003 | Hill et al. |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0010303 A1 | 1/2004 | Bolea et al. |
| 2004/0015204 A1 | 1/2004 | Whitehurst et al. |
| 2004/0015205 A1 | 1/2004 | Whitehurst et al. |
| 2004/0019364 A1 | 1/2004 | Kieval et al. |
| 2004/0024422 A1 | 2/2004 | Hill et al. |
| 2004/0030362 A1 | 2/2004 | Hill et al. |
| 2004/0038857 A1 | 2/2004 | Tracey |
| 2004/0048795 A1 | 3/2004 | Ivanova et al. |
| 2004/0049120 A1 | 3/2004 | Cao et al. |
| 2004/0049235 A1 | 3/2004 | Deno et al. |
| 2004/0054381 A1 | 3/2004 | Pastore et al. |
| 2004/0059383 A1 | 3/2004 | Puskas |
| 2004/0068299 A1 | 4/2004 | Laske et al. |
| 2004/0088009 A1 | 5/2004 | Degroot |
| 2004/0088015 A1 | 5/2004 | Casavant et al. |
| 2004/0111118 A1 | 6/2004 | Hill et al. |
| 2004/0116970 A1 | 6/2004 | Girouard et al. |
| 2004/0122496 A1 | 6/2004 | Zhang et al. |
| 2004/0122497 A1 | 6/2004 | Zhang et al. |
| 2004/0122498 A1 | 6/2004 | Zhang et al. |
| 2004/0127942 A1 | 7/2004 | Yomtov et al. |
| 2004/0127947 A1 | 7/2004 | Kim et al. |
| 2004/0133248 A1 | 7/2004 | Frei et al. |
| 2004/0138721 A1 | 7/2004 | Osorio et al. |
| 2004/0162584 A1 | 8/2004 | Hill et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0172094 A1 | 9/2004 | Cohen et al. |
| 2004/0186517 A1 | 9/2004 | Hill et al. |
| 2004/0186531 A1 | 9/2004 | Jahns et al. |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0215289 A1 | 10/2004 | Fukui |
| 2004/0220621 A1 | 11/2004 | Zhou et al. |
| 2004/0243182 A1 | 12/2004 | Cohen et al. |
| 2004/0243206 A1 | 12/2004 | Tadlock |
| 2004/0249416 A1 | 12/2004 | Yun et al. |
| 2004/0249429 A1 | 12/2004 | Tadlock |
| 2004/0254612 A1 | 12/2004 | Ezra et al. |
| 2004/0254616 A1 | 12/2004 | Rossing et al. |
| 2004/0260374 A1 | 12/2004 | Zhang et al. |
| 2004/0260375 A1 | 12/2004 | Zhang et al. |
| 2005/0010263 A1* | 1/2005 | Schauerte ................... 607/48 |
| 2005/0015129 A1 | 1/2005 | Mische |
| 2005/0021092 A1 | 1/2005 | Yun et al. |
| 2005/0059897 A1 | 3/2005 | Snell et al. |
| 2005/0065553 A1 | 3/2005 | Ben Ezra et al. |
| 2005/0065555 A1 | 3/2005 | Er |
| 2005/0065562 A1 | 3/2005 | Rezai |
| 2005/0065573 A1 | 3/2005 | Rezai |
| 2005/0065575 A1 | 3/2005 | Dobak |
| 2005/0075701 A1 | 4/2005 | Shafer |
| 2005/0075702 A1 | 4/2005 | Shafer |
| 2005/0085864 A1 | 4/2005 | Schulman et al. |
| 2005/0096705 A1 | 5/2005 | Pastore et al. |
| 2005/0096707 A1 | 5/2005 | Hill et al. |
| 2005/0125044 A1 | 6/2005 | Tracey |
| 2005/0131467 A1 | 6/2005 | Boveja |
| 2005/0143412 A1 | 6/2005 | Puskas |
| 2005/0143779 A1 | 6/2005 | Libbus |
| 2005/0143785 A1 | 6/2005 | Libbus |
| 2005/0143787 A1 | 6/2005 | Boveja et al. |
| 2005/0149126 A1 | 7/2005 | Libbus |
| 2005/0149127 A1 | 7/2005 | Libbus |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149148 A1 | 7/2005 | King |
| 2005/0149156 A1 | 7/2005 | Libbus et al. |
| 2005/0154418 A1* | 7/2005 | Kieval et al. ................ 607/2 |
| 2005/0182288 A1 | 8/2005 | Zabara |
| 2005/0187584 A1 | 8/2005 | Denker et al. |
| 2005/0187586 A1 | 8/2005 | David et al. |
| 2005/0197600 A1 | 9/2005 | Schuler et al. |
| 2005/0197675 A1 | 9/2005 | David et al. |
| 2005/0222632 A1 | 10/2005 | Obino |
| 2005/0251216 A1 | 11/2005 | Hill et al. |
| 2005/0261741 A1 | 11/2005 | Libbus et al. |
| 2006/0074453 A1 | 4/2006 | Kieval et al. |
| 2006/0079945 A1 | 4/2006 | Libbus |
| 2006/0089678 A1 | 4/2006 | Shalev |
| 2006/0106428 A1 | 5/2006 | Libbus et al. |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0134071 A1 | 6/2006 | Ross et al. |

| | | | |
|---|---|---|---|
| 2006/0134079 A1 | 6/2006 | Sih et al. |
| 2006/0136027 A1 | 6/2006 | Westlund et al. |
| 2006/0136028 A1 | 6/2006 | Ross et al. |
| 2006/0217772 A1 | 9/2006 | Libbus et al. |
| 2006/0253156 A1 | 11/2006 | Pastore et al. |
| 2006/0259107 A1 | 11/2006 | Caparso et al. |
| 2006/0271115 A1 | 11/2006 | Ben-Ezra et al. |
| 2006/0271118 A1 | 11/2006 | Libbus et al. |
| 2006/0282131 A1 | 12/2006 | Caparso et al. |
| 2007/0021790 A1 | 1/2007 | Kieval et al. |
| 2007/0021792 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0034261 A1 | 2/2007 | Eichler |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0060972 A1 | 3/2007 | Kieval et al. |
| 2007/0067008 A1 | 3/2007 | Scheiner et al. |
| 2007/0068260 A1 | 3/2007 | Hong et al. |
| 2007/0093875 A1 | 4/2007 | Chavan et al. |
| 2007/0142864 A1 | 6/2007 | Libbus et al. |
| 2007/0142871 A1 | 6/2007 | Libbus et al. |
| 2007/0167984 A1 | 7/2007 | Kieval et al. |
| 2007/0191904 A1 | 8/2007 | Libbus et al. |
| 2008/0021507 A1 | 1/2008 | Libbus et al. |
| 2008/0086174 A1 | 4/2008 | Libbus et al. |
| 2008/0125843 A1 | 5/2008 | Ben-David et al. |
| 2008/0147140 A1 | 6/2008 | Ternes et al. |
| 2008/0167694 A1 | 7/2008 | Bolea et al. |
| 2008/0177350 A1 | 7/2008 | Kieval et al. |
| 2008/0200960 A1 | 8/2008 | Libbus |
| 2008/0228238 A1 | 9/2008 | Libbus |
| 2009/0048641 A1 | 2/2009 | Libbus |
| 2009/0132002 A1 | 5/2009 | Kieval |
| 2009/0143834 A1 | 6/2009 | Libbus |
| 2009/0143838 A1 | 6/2009 | Libbus et al. |
| 2009/0198294 A1 | 8/2009 | Rossing et al. |
| 2009/0306734 A1 | 12/2009 | Moffitt et al. |
| 2010/0076511 A1 | 3/2010 | Heil, Jr. et al. |
| 2010/0106226 A1 | 4/2010 | Libbus |
| 2010/0125307 A1 | 5/2010 | Pastore et al. |
| 2010/0185255 A1 | 7/2010 | Libbus |
| 2010/0222832 A1 | 9/2010 | Zhang et al. |
| 2010/0274321 A1 | 10/2010 | Libbus |
| 2010/0286740 A1 | 11/2010 | Libbus et al. |
| 2010/0298898 A1 | 11/2010 | Libbus |
| 2011/0082514 A1 | 4/2011 | Libbus et al. |
| 2011/0106216 A1 | 5/2011 | Libbus et al. |

FOREIGN PATENT DOCUMENTS

| | | | |
|---|---|---|---|
| EP | 1486232 A2 | 12/2004 |
| EP | 1541193 A1 | 6/2005 |
| EP | 1706177 A1 | 10/2006 |
| GB | 1297991 | 11/1972 |
| JP | 49015438 | 4/1974 |
| JP | 05269210 | 10/1993 |
| JP | 2004526471 | 9/2004 |
| JP | 2005519680 | 7/2005 |
| JP | 2005521489 | 7/2005 |
| WO | WO-9216257 A1 | 4/1997 |
| WO | WO-9713550 A1 | 4/1997 |
| WO | WO-9740885 A1 | 11/1997 |
| WO | WO-0124876 A1 | 4/2001 |
| WO | WO-0176689 A2 | 10/2001 |
| WO | WO-0226314 A1 | 4/2002 |
| WO | WO-0226318 A1 | 4/2002 |
| WO | WO-0226320 A1 | 4/2002 |
| WO | WO-0234327 A2 | 5/2002 |
| WO | WO-02085448 A2 | 10/2002 |
| WO | WO 03/011388 * | 2/2003 |
| WO | WO-03026741 A1 | 4/2003 |
| WO | WO-03041559 A2 | 5/2003 |
| WO | WO-03076008 A1 | 9/2003 |
| WO | WO-03082080 A2 | 10/2003 |
| WO | WO-03082080 A3 | 10/2003 |
| WO | WO-03082403 A2 | 10/2003 |
| WO | WO-03099373 A2 | 12/2003 |
| WO | WO-03099377 A1 | 12/2003 |
| WO | WO-2004012814 A1 | 2/2004 |
| WO | WO-2004084990 A1 | 10/2004 |
| WO | WO-2004084993 A1 | 10/2004 |
| WO | WO-2004103455 A2 | 12/2004 |
| WO | WO-2004105870 A1 | 12/2004 |
| WO | WO-2004110549 A2 | 12/2004 |
| WO | WO-2004110550 A2 | 12/2004 |
| WO | WO-2005018739 A1 | 3/2005 |
| WO | WO-2005042091 A1 | 5/2005 |
| WO | WO-2005053788 A1 | 6/2005 |
| WO | WO-2005063332 A1 | 7/2005 |
| WO | WO-2005065771 A1 | 7/2005 |
| WO | WO-2005113066 A1 | 12/2005 |
| WO | WO-2006031331 A1 | 3/2006 |
| WO | WO-2007/078410 A1 | 7/2007 |
| WO | WO-2008063396 A1 | 5/2008 |

OTHER PUBLICATIONS

Chapleau, M W., et al., "Neuro-cardiovascular regulation: from molecules to man. Introduction.", *Annals of the New York Academy of Sciences*, 940, (Jun. 2001),xiii-xxii.

Chapleau, M W., et al., "Pulsatile activation of baroreceptors causes central facilitation of baroreflex", *American Journal of Physiology*, 256(6 Pt 2), (Jun. 1989),H1735-41.

Dickerson, L W., "Parasympathetic neurons in the cranial medial ventricular fat pad on the dog heart selectively decrease ventricular contractility" *Journal of the Autonomic Nervous System*, 70(1-2), (May 28, 1998),129-41.

Diedrich, A , et al., "Analysis of raw microneurographic recordings based on wavelet de-noising technique and classification algorithm: wavelet analysis in microneurography", *IEEE Transactions on Biomedical Engineering*, 50(1), (Jan. 2003),41-50.

Gatti, P J., "Vagal control of left ventricular contractility is selectively mediated by a cranioventricular intracardiac ganglion in the cat", *Journal of the Autonomic Nervous System*, 66(3), Oct. 13, 1997 , 138-44.

Holder, L K., "Treatment of refractory partial seizures: preliminary results of a controlled study", *Pacing & Clinical Electrophysiology*, 15(10 Pt 2), (Oct. 1992),1557-71.

Kendrick, J E., et al., "A comparison of the cardiovascular responses to stimulation of the aortic and carotid sinus nerves of the dog", *Proceedings of the Society for Experimental Biology & Medicine*, 144(2), (Nov. 1973),404-11.

Libbus, Imad , "Baroreflex Modulation Based on Monitored Cardiovascular Parameter", U.S. Appl. No. 10/939,544, filed Sep. 13, 2004, 75 pgs.

Libbus, Imad , "Baroreflex Therapy for Disordered Breathing", U.S. Appl. No. 10/864,070, filed Jun. 8, 2004, 71 pgs.

Libbus, I. , et al., "Integrated Lead for Applying Cardiac Resynchronization Therapy and Neural Stimulation Therapy", U.S. Appl. No. 11/077,970, filed Mar. 11, 2005, 67 pgs.

Libbus, I. , et al., "Method and Apparatus for Synchronizing Neural Simulation to Cardiac Cycles", U.S. Appl. No. 11/099,141, filed Apr. 5, 2005.

Libbus, I. , et al., "System and Method for Closed-Loop Neural Stimulation", U.S. Appl. No. 10/992,319, filed Nov. 18, 2004.

Moffitt, Julia , et al., "Combined Neural Stimulation and Cardiac Resynchronization Therapy", U.S. Appl. No. 11/078,460, filed Mar. 11, 2005, 35 pgs.

Nolan, J , "Prospective study of heart rate variability and mortality in chronic heart failure: results of the United Kingdom heart failure evaluation and assessment of risk trial (UK-heart).", *Circulation*, 98(15), (Oct. 13, 1998),1510-6.

Schmidt, E M., "Blood pressure response to aortic nerve stimulation in swine", *American Journal of Physiology*, 215(6), (Dec. 1968),1488-92.

Sigurdsson, A , "The role of neurohormonal activation in chronic heart failure and postmyocardial infarction", *American Heart Journal*, 132(1 Pt 2 Su), (Jul. 1996),229-34.

Thompson, G W., et al., "Bradycardia induced by intravascular versus direct stimulation of the vagus nerve", *Annals of Thoracic Surgery*, 65(3), (Mar. 1998),637-42.

Zamotrinsky, A V., et al., "Vagal neurostimulation in patients with coronary artery disease", *Autonomic Neuroscience-Basic & Clinical*, 88(1-2), (Apr. 12, 2001),109-16.

"http://www.cardioconsult.com/Anatomy/", http://www.cardioconsult.com/Anatomy/, (2003),4.

American Heart Association, "Hypertension Population Statistics", (2002),1 pg.

Andersen, H , "Long-term follow-up of patients from a randomised trial of atrial versus ventricular pacing for sick-sinus syndrome", *Lancet*, 350(9086), (Oct. 25, 1997),1210-6.

Benchimol, A , "Cardiac hemodynamics during stimulation of the right atrium, right ventricle, and left ventricle in normal and abnormal hearts", *Circulation*, 33(6), (Jun. 1966),933-44.

Bevan, J A., et al., "Postganglionic sympathetic delay in vascular smooth muscle", *Journal of Pharmacology & Experimental Therapeutics*, 152(2), (May 1966),221-30.

Bevan, J A., et al., "Sympathetic nerve-free vascular muscle", *Journal of Pharmacology & Experimental Therapeutics*, 157(1), (Jul. 1967),117-24.

Bilgutay, A M., et al., "A new concept in the treatment of hypertension utilizing an implantable electronic device: "Baropacer"", *Trans Am Soc Artif Intern Organs.*, 10, (1964),387-95.

Bilgutay, A M., et al., "Vagal tuning for the control of supraventricular arrhythmias", *Surgical Forum*, 16, (1965),151-3.

Bilgutay, Aydin M., "Vagal tuning. A new concept in the treatment of supraventricular arrhythmias, angina pectoris, and heart failure" *Journal of Thoracic and Cardiovascular Surgery*, 56(1), (Jul. 1968),71-82.

Borst, C , et al., "Optimal frequency of carotid sinus nerve stimulation in treatment of angina pectoris", *Cardiovascular Research*. 8(5), (Sep. 1974),674-80.

Braunwald, E , et al., "Carotid sinus nerve stimulation in the treatment of angina pectoris and supraventricular tachycardia", *California Medicine*, 112(3), (Mar. 1970),41-50.

Braunwald, E , et al., "Relief of angina pectoris by electrical stimulation of the carotid-sinus nerves", *New England Journal of Medicine*, 277(24), (Dec. 14, 1967),1278-83.

Coleridge, J C., et al., "Relationship between pulmonary arterial pressure and impulse activity in pulmonary arterial baroreceptor fibres", *Journal of Physiology*, 158 (Sep. 1961),197-205.

Coleridge, J C., et al., "The distribution, connexions and histology of baroreceptors in the pulmonary artery, with some observations on the sensory innervation of the ductus arteriosus", *Journal of Physiology*, 156, (May 1961),591-602.

Cooper, T B., et al., "Neural effects on sinus rate and atrioventricular conduction produced by electrical stimulation from a transvenous electrode catheter in the canine right pulmonary artery", *Circulation Research*, 46(1), (Jan. 1980),48-57.

Courtice, G P., et al., "Effect of frequency and impulse pattern on the non-cholinergic cardiac response to vagal stimulation in the toad, Bufo marinus", *Journal of the Autonomic Nervous System*, 48(3), (Aug. 1994),267-72.

Dart Jr., C H., et al., "Carotid sinus nerve stimulation treatment of angina refractory to other surgical procedures", *Annals of Thoracic Surgery*, 11(4), (Apr. 1971),348-59.

De Landsheere, D , et al., "Effect of spinal cord stimulation on regional myocardial perfusion assessed by positron emission tomography", *American Journal of Cardiology*, 69(14), (May 1, 1992),1143-9.

Dunning, Arend J., "Electrostimulation of the Carotid Sinus Nerve in Angina Pectoris", *University Department of Medicine*, Binnengasthuis, Amsterdam; Printed by Royal VanGorcum, Assen, Netherlands, (1971),1-92.

Epstein, S E., et al., "Treatment of angina pectoris by electrical stimulation of the carotid-sinus nerves", *New England Journal of Medicine*, 280(18), (May 1, 1969),971-8.

Farrehi, C , "Stimulation of the carotid sinus nerve in treatment of angina pectoris", *American Heart Journal*, 80(6), (Dec. 1970),759-65.

Feliciano, L , et al., "Vagal nerve stimulation releases vasoactive intestinal peptide which significantly increases coronary artery blood flow", *Cardiovascular Research*, 40(1), (Oct. 1998),45-55.

Fromer, M , et al., "Ultrarapid subthreshold stimulation for termination of atrioventricular node reentrant tachycardia", *Journal of the American College of Cardiology*, 20(4), (Oct. 1992),879-83.

Grassi, Guido , et al., "Baroreflex and non-baroreflex modulation of vagal cardiac control after myocardial infarction", *Am J Cardiol.*, 84(5), (Sep. 1, 1999),525-9.

Griffith, Lawrence S., et al., "Electrical Stimulation of the Carotid Sinus Nerve in Normotensive and Renal Hypertensive Dogs", *Circulation*, 28, (Jul.-Dec. 1963),730.

Heil, Jr., Ronald W., et al., "Barorelflex Stimulation System to Reduce Hypertension", U.S. Appl. No. 10/746,134, filed Dec. 24, 2003, 78 pgs.

Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Henning, R J., et al., "Vagal nerve stimulation increases right ventricular contraction and relaxation and heart rate", *Cardiovascular Research*, 32(5),(Nov. 1996),846-53.

Henning, R J., et al., "Vagal stimulation attenuates sympathetic enhancement of left ventricular function", *American Journal of Physiology*, 258(5 Pt 2), (May 1990),H1470-5

Hood Jr., W B., et al., "Asynchronous contraction due to late systolic bulging at left ventricular pacing sites", *American Journal of Physiology*, 217(1), (Jul. 1969),215-21.

Ishise, H , "Time course of sympathovagal imbalance and left ventricular dysfunction in conscious dogs with heart failure", *Journal of Applied Physiology*,84(4), (Apr. 1998),1234-41.

Jessurun, G A., et al., "Coronary blood flow dynamics during transcutaneous electrical nerve stimulation for stable angina pectoris associated with severe narrowing of one major coronary artery", *American Journal of Cardiology*, erratum appears in Am J Cardiol Feb. 15, 1999;83(4):642,(Oct. 15, 1998),921-6.

Kandel, Eric R., et al., "Part VII: Arousal, Emotion, and Behavioral Homeostasis", *In: Principles of neural science*, New York : McGraw-Hill, Health Professions Division,(2000),966-969.

Karpawich, P P., et al., "Altered cardiac histology following apical right ventricular pacing in patients with congenital atrioventricular block", *Pacing Clin Electrophysiol*, 22(9), (Sep. 1999),1372-7.

Leclercq, C , et al., "Hemodynamic importance of preserving the normal sequence of ventricular activation in permanent cardiac pacing", *Am Heart J.*, 129(6), (Jun. 1995),1133-41.

Libbus, Imad , "Automatic Baroreflex Modulation Based on Cardiac Activity", U.S. Appl. No. 10/746,846, filed Dec. 24, 2003, 83 pgs.

Libbus, Imad , "Automatic Baroreflex Modulation Responsive to Adverse Event", U.S. Appl. No. 10/745,925, filed Dec. 24, 2003, 81 pgs.

Libbus, Imad , et al., "Baropacing and Cardiac Pacing to Control Output", U.S. Appl. No. 10/746,135, filed Dec. 24, 2003, 79 pgs.

Libbus, Imad , et al., "Baroreflex Modulation to Gradually Decrease Blood Pressure", U.S. Appl. No. 10/746,845, filed Dec. 24, 2003, 83 pgs.

Libbus, Imad , "Baroreflex Stimulation Synchronized to Circadian Rhythm", U.S. Appl. No. 10/746,844, filed Dec. 24, 2003, 78 pgs.

Libbus, Imad , "Baroreflex Stimulation to Treat Acute Myocardial Infarction", U.S. Appl. No. 10/745,920, filed Dec. 24, 2003, 78 pgs.

Libbus, Imad , "Baroreflex Stimulator With Integrated Pressure Sensor", U.S. Appl. No. 10/745,921, filed Dec. 24, 2003, 80 pgs.

Libbus, Imad , et al., "Lead for Stimulating the Baroreceptors in the Pulmonary Artery", U.S. Appl. No. 10/746,861, filed Dec. 24, 2003, 21 pgs.

Libbus, Imad , et al., "Sensing With Compensation for Neural Stimulator", U.S. Appl. No. 10/746,847, filed Dec. 24, 2003, 79 pgs.

Mannheimer, C , et al., "Epidural spinal electrical stimulation in severe angina pectoris", *British Heart Journal*, 59(1), (Jan. 1988),56-61.

Mannheimer, C , et al., "Transcutaneous electrical nerve stimulation (TENS) in angina pectoris", *Pain*, 26(3), (Sep. 1986),291-300.

Mannheimer, C , et al., "Transcutaneous electrical nerve stimulation in severe angina pectoris", *European Heart Journal*, 3(4), (Aug. 1982),297-302.

Mazgalev, T N., et al., "Autonomic modification of the atrioventricular node during atrial fibrillation: role in the slowing of ventricular rate", *Circulation*, 99(21), (Jun. 1, 1999),2806-14.

Millar-Craig, M W., et al., "Circadian variation of blood-pressure", *Lancet*, 1(8068), (Apr. 15, 1978),795-7.

Minisi, A J., et al., "Regional left ventricular deafferentation increases baroreflex sensitivity following myocardial infarction", *Cardiovasc Res.*, 58(1), (Apr. 1, 2003),136-41.

Murphy, D F., et al., "Intractable angina pectoris: management with dorsal column stimulation", *Medical Journal of Australia*, 146(5), (Mar. 2, 1987),260.

Neistadt, A , et al., "Effects of electrical stimulation of the carotid sinus nerve in reversal of experimentally induced hypertension", *Surgery*, 61(6), (Jun. 1967),923-31.

Pastore, Joseph M., et al., "Multi-Site Ventricular Pacing Therapy With Parasympathetic Stimulation", U.S. Appl. No. 10/700,368, filed Nov. 3, 2003, 18 pgs.

Peters, T K., et al., "Temporal and spatial summation caused by aortic nerve stimulation in rabbits. Effects of stimulation frequencies and amplitudes", *Journal of the Autonomic Nervous System*, 27(3), (Aug. 1989),193-205.

Peters, T K., et al., "The principle of electrical carotid sinus nerve stimulation: a nerve pacemaker system for angina pectoris and hypertension therapy", *Annals of Biomedical Engineering*, 8(4-6), 1980,445-58.

Philbin, D M., et al., "Inappropriate shocks delivered by an ICD as a result of sensed potentials from a transcutaneous electronic nerve stimulation unit", *Pacing & Clinical Electrophysiology*, 21(10), (Oct. 1998),2010-1.

Prakash, P , et al., "Asymmetrical distribution of aortic nerve fibers in the pig", *Anat Rec.*, 158(1), (May 1967),51-7.

Rosenqvist, M , "The effect of ventricular activation sequence on cardiac performance during pacing", *Pacing and Electrophysiology*, 19(9), (1996),1279-1286.

Rushmer, Robert F., "Chapter 5—Systemic Arterial Pressure", In: *Cardiovascular dynamics*, Philadelphia : Saunders,(1976),176-216.

Schauerte, P , et al., "Catheter stimulation of cardiac parasympathetic nerves in humans: a novel approach to the cardiac autonomic nervous system", *Circulation*, 104(20), (Nov. 13, 2001),2430-5.

Schauerte, P N., et al., "Transvenous parasympathetic cardiac nerve stimulation: an approach for stable sinus rate control", *Journal of Cardiovascular Electrophysiology*, 10(11), (Nov. 1999),1517-24.

Schauerte, P , "Transvenous Parasympathetic Nerve Stimulation in the Inferior Vena Cava and Atrioventricular Conduction", *Journal of Cardiovascular Electrophysiology*, 11(1), (Jan. 2000),64-69.

Schauerte, P , et al., "Ventricular rate control during atrial fibrillation by cardiac parasympathetic nerve stimulation: a transvenous approach", *Journal of the American College of Cardiology*, 34(7), (Dec. 1999),2043-50.

Scherlag, M A., "Endovascular Neural Stimulation Via a Novel Basket Electrode Catheter: Comparison of Electrode Configurations", *Journal of Interventional Cardiac Electrophysiology*, 4(1), (Apr. 2000),219-224.

Takahashi, N , "Vagal modulation of ventricular tachyarrhythmias induced by left ansae subclaviae stimulation in rabbits", *Japanese Heart Journal*, 39(4), (Jul. 1998),503-11.

Tse, H F., et al., "Long-term effect of right ventricular pacing on myocardial perfusion and function", *J Am Coll Cardiol.*, 29(4), (Mar. 15, 1997),744-9.

Vanoli, E , "Vagal stimulation and prevention, of sudden death in conscious dogs with a healed myocardial infarction", *Circulation Research*, 68(5), (May 1991),1471-81.

Veerman, D P., et al., "Circadian profile of systemic hemodynamics", *Hypertension*, 26(1), (Jul. 1995),55-9.

Verity, M A., et al., "Plurivesicular nerve endings in the pulmonary artery", *Nature*, 211(48) (Jul. 30, 1966),537-8.

Verity, M , et al., "Pulmonary artery innervation: a morphopharmacologic correlation", *Proceedings of the Western Pharmacology Society*, 8, (1965),57-9.

Wallick, D W., "Selective AV nodal vagal stimulation improves hemodynamics during acute atrial fibrillation in dogs", *American Journal of Physiology—Heart & Circulatory Physiology*, (Oct. 2001),H1490-7.

Waninger, M S., et al., "Electrophysiological control of ventricular rate during atrial fibrillation", *Pacing & Clinical Electrophysiology*, 23(8), (Aug. 2000),1239-44.

Wiggers, C J., et al., "The muscular reactions of the mammalian ventricles to artificial surface stimuli", *American Journal of Physiology*, (1925),346-378.

Zhang, Y , et al., "Optimal ventricular rate slowing during atrial fibrillation by feedback AV nodal-selective vagal stimulation", *American Journal of Physiology—Heart & Circulatory Physiology*, 282(3), (Mar. 2002),H1102-10.

Zhou, X , et al., "Prevention of high incidence of neurally mediated ventricular arrhythmias by afferent nerve stimulation in dogs", *Circulation*, 101(7), (Feb. 22, 2000),819-24.

Chapleau, Mark W., "Contrasting effects of static and pulsatile pressure carotid baroreceptor activity in dogs", *Circulation*, vol. 61, No. 5, (Nov. 1987), 648-658.

Li, Meihua, "Vagal nerve stimulation markedly improves long-term survival after chronic heart failure in rats", *Circulation*, 109(1), Epub Dec. 8, 2003,(Jan. 6, 2004), 1-5.

Libbus, Imad, "Cardiac Rhythm Management Device with Neural Sensor", U.S. Appl. No. 10/992,320, filed Nov. 18, 2004, 65 pgs.

Libbus, Imad, "Neural Stimulation with Avoidance of Inappropriate Stimulation", U.S. Appl. No. 11/000,249, filed Nov. 30, 2004, 45 pgs.

Libbus, Imad, "Stimulator for Auricular Branch of Vagus Nerve", U.S. Appl. No. 11/005,703, filed Dec. 7. 2004, 35 pgs.

Libbus, Imad, "System and Method for Sustained Baroreflex Stimulation", U.S. Appl. No. 10/962,845, filed Oct. 12, 2004, 50 Pages.

Libbus, Imad, "System to Provide Myocardial and Neural Stimulation", U.S. Appl. No. 11/087,935, filed Mar. 23, 2005, 52 pgs.

Zarse, Markus, et al., "Selective Increase of Cardiac Neuronal Sympathetic Tone—A Catheter-Based Access to Modulate Left Ventricular Contractility", *Journal of the American College Cardiology*, 46(7), (Oct. 4, 2005), 1354-1359.

Non-Final Office Action mailed by the USPTO on Apr. 26, 2007 for related matter U.S. Appl. No. 10/746,846, 18 Pages.

"Devices and Methods for Cardiovascular Reflex Control", U.S. Appl. No. 60/368,222, filed Mar. 27, 2002, 146 Pages.

"Non-Final Office Action mailed Jul. 12, 2007 in U.S. Appl. No. 10/746,861", OARN,21 pgs.

"Preliminary Statement U.S. Appl. No. 11/482,225 dated Oct. 31, 2006", 2 Pages.

"Preliminary Statement U.S. Appl. No. 11/482,453 dated Oct. 31, 2006", 3 Pages.

"Preliminary Statement U.S. Appl. No. 11/482,635, Dated Oct. 31, 2006", 2 Pages.

"Preliminary Statement U.S. Appl. No. 11/482,662 dated Oct. 31, 2006", 2 Pages.

Coleridge, J. C., et al., "Reflex effects of stimulating baroreceptors in the pulmonary artery", *J. Physiol*, 166, (1963),197-210.

Kieval, Robert , et al., "Devices and Methods for Cardiovascular Reflex Control", U.S. Appl. No. 10/284,063, filed Oct. 29, 2002, 52 Pages.

Libbus, Imad , "Automatic Neural Stimulation Modulation Based on Activity", U.S. Appl. No. 11/558,083, filed Nov. 9, 2006.

Libbus, Imad , et al., "Sensing With Compensation for Neural Stimulator", U.S. Appl. No. 11/621,194, filed Jan. 9, 2007, 69 pgs.

McGregor, A. , et al., "Right-Sided Vagus Nerve Stimulation as a Treatment for Refractory Epilepsy in Humans", *Epilepsia*; 46(1), (Jan. 2005),91-96.

"U.S. Appl. No. 10/746,861, Notice of Appeal filed Apr. 24, 2007", 1 pg.

"U.S. Appl. No. 10/746,861, Response filed Dec. 12, 2007 to Non-Final Office Action mailed Jul. 12, 2007", 13 pgs.

"U.S. Appl. No. 10/746,861 Final Office Action mailed Oct. 24, 2006", 20 pgs.

"U.S. Appl. No. 10/746,861 Non Final Office Action mailed Apr. 6, 2006", 22 pgs.

"U.S. Appl. No. 10/746,861 Response filed Jan. 24, 2007 to Final Office Action mailed Oct. 24, 2006", 12 pgs.

"U.S. Appl. No. 10/746,861 Response filed Jun. 25, 2007 to Advisory Action mailed Jan. 31, 2007", 12 pgs.

"U.S. Appl. No. 10/746,861 Response filed Aug. 7, 2006 to Non Final Office Action mailed Apr. 6, 2006", 13 pgs.

"U.S. Appl. No. 10/746,861, Advisory Action mailed Jan. 31, 2007", 3 pgs.

Chavan, Abhi, et al., "Implantable and Rechargeable Neural Stimulator", U.S. Appl. No. 11/256,907, filed Oct. 24, 2005, 35 Pages.

Janes, R. D., "Anatomy of human extrinsic cardiac nerves and ganglia.", *Am J Cardio.*, 57(4), Feb. 1, 1986, 299-309.

Libbus, Imad, "Implantable Device for Treating Epilepsy and Cardiac Rhythm Disorders", U.S. Appl. No. 11/312,178, filed Dec. 21, 2005, 39 Pages.

Scherlag, B. J., "Endovascular stimulation within the left pulmonary artery to induce slowing of heart rate and paroxysmal atrial fibrillation.", *Cardiovasc Research*, 54(2), (May 2002), 470-475.

"U.S. Appl. No. 10/700,368, Final Office Action mailed Oct. 15, 2008", 12 pgs.

"U.S. Appl. No. 10/700,368, Non-Final Office Action mailed Feb. 25, 2009", 13 pgs.

"U.S. Appl. No. 10/700,368, Non-Final Office Action mailed Mar. 14, 2008", 13 pgs.

"U.S. Appl. No. 10/700,368, Notice of Allowance mailed Sep. 15, 2009", 7 pgs.

"U.S. Appl. No. 10/700,368, Response filed Jan. 15, 2009 to Final Office Action mailed Oct. 15, 2008", 8 pgs.

"U.S. Appl. No. 10/700,368, Response filed Jan. 31, 2008 to Final Office Action mailed Oct. 31, 2007", 8 pgs.

"U.S. Appl. No. 10/700,368, Response filed Jun. 16, 2008 to Non-Final Office Action mailed Mar. 14, 2008", 8 pgs.

"U.S. Appl. No. 10/700,368, Response filed Jul. 20, 2009 to Non Final Office Action mailed Feb. 25, 2009", 11 pgs.

"U.S. Appl. No. 10/745,920, Notice of Allowance mailed Jul. 29, 2008", 8 pgs.

"U.S. Appl. No. 10/745,920, Response filed Apr. 16, 2008 to Restriction Requirement mailed Mar. 17, 2008", 8 pgs.

"U.S. Appl. No. 10/745,920, Response filed Sep. 4, 2007 to Restriction Requirement mailed Aug. 1, 2007", 5 pgs.

"U.S. Appl. No. 10/745,920, Restriction Requirement mailed Mar. 17, 2008", 7 pgs.

"U.S. Appl. No. 10/745,921, Appeal Brief filed Apr. 23, 2007", 38 pgs.

"U.S. Appl. No. 10/745,921, Appeal Brief filed Jul. 13, 2007", 37 pgs.

"U.S. Appl. No. 10/745,921, Decision on Appeal mailed Sep. 3, 2008", 18 pgs.

"U.S. Appl. No. 10/745,921, Examiner Interview Summary mailed Mar. 24, 2010", 3 pgs.

"U.S. Appl. No. 10/745,921, Examiner's Answer mailed Sep. 27, 2007", 17 pgs.

"U.S. Appl. No. 10/745,921, Final Office Action mailed Jan. 24, 2010", 16 pgs.

"U.S. Appl. No. 10/745,921, Non-Final Office Action mailed Jul. 27, 2009", 15 pgs.

"U.S. Appl. No. 10/745,921, Notice of Allowance mailed Sep. 7, 2010", 6 pgs.

"U.S. Appl. No. 10/745,921, Notification mailed Jun. 5, 2007", 2 pgs.

"U.S. Appl. No. 10/745,921, Reply Brief filed Nov. 27, 2007", 31 pgs.

"U.S. Appl. No. 10/745,921, Response filed Feb. 21, 2006 to Restriction Requirement mailed Jan. 19, 2006", 15 pgs.

"U.S. Appl. No. 10/745,921, Response filed May 6, 2009 to Restriction Requirement mailed Jan. 6, 2009", 12 pgs.

"U.S. Appl. No. 10/745,921, Response filed Jun. 14, 2010 to Final Office Action mailed Jan. 14, 2010", 16 pgs.

"U.S. Appl. No. 10/745,921, Response filed Oct. 27, 2009 to Non-Final Office Action mailed Jul. 27, 2009", 16 pgs.

"U.S. Appl. No. 10/745,921, Restriction Requirement mailed Jan. 6, 2009", 9 pgs.

"U.S. Appl. No. 10/745,921, Restriction Requirement mailed Jan. 19, 2006", 5 pgs.

"U.S. Appl. No. 10/745,921, Supplemental Notice of Allowability mailed Nov. 1, 2010", 4 pgs.

"U.S. Appl. No. 10/745,925, Final Office Action mailed Jan. 1, 2008", 11 pgs.

"U.S. Appl. No. 10/745,925, Non-Final Office Action mailed May 1, 2008", 13 pgs.

"U.S. Appl. No. 10/745,925, Notice of Allowance mailed Nov. 14, 2008", 6 pgs.

"U.S. Appl. No. 10/745,925, Response filed Apr. 11, 2008 to Final Office Action mailed Jan. 11, 2008", 14 pgs.

"U.S. Appl. No. 10/745,925, Response filed Aug. 1, 2008 to Non Final Office Action mailed May 1, 2008", 11 pgs.

"U.S. Appl. No. 10/745,925, Response filed Oct. 17, 2007 to Restriction Requirement mailed Sep. 18, 2007", 8 pgs.

"U.S. Appl. No. 10/746,134, Final Office Action mailed Feb. 21, 2008", 10 pgs.

"U.S. Appl. No. 10/746,134, Final Office Action mailed Jul. 10, 2008", 10 pgs.

"U.S. Appl. No. 10/746,134, Non-Final Office Action mailed Feb. 6, 2009", 10 pgs.

"U.S. Appl. No. 10/746,134, Response filed Jul. 6, 2009 to Non-Final Office Action mailed Feb. 6, 2009", 16 pgs.

"U.S. Appl. No. 10/746,134, Response filed Dec. 10, 2008 to Final Office Action mailed Jul. 10, 2008", 11 pgs.

"U.S. Appl. No. 10/746,134, Supplemental Notice of Allowability mailed Aug. 31, 2009", 5 pgs.

"U.S. Appl. No. 10/746,135, Appeal Brief mailed May 10, 2010", 43 pgs.

"U.S. Appl. No. 10/746,135, Decision on Pre-Appeal Brief mailed Mar. 10, 2010", 2 pgs.

"U.S. Appl. No. 10/746,135, Examiner Interview Summary mailed Feb. 6, 2009", 8 pgs.

"U.S. Appl. No. 10/746,135, Examiner's Answer mailed Jul. 22, 2010", 17 pgs.

"U.S. Appl. No. 10/746,135, Final Office Action mailed Mar. 18, 2008", 16 pgs.

"U.S. Appl. No. 10/746,135, Final Office Action mailed Jul. 22, 2009", 14 pgs.

"U.S. Appl. No. 10/746,135, Non-Final Office Action mailed Sep. 30, 2008", 18 pgs.

"U.S. Appl. No. 10/746,135, Pre-Appeal Brief Request filed Dec. 21, 2009", 5 pgs.

"U.S. Appl. No. 10/746,135, Reply Brief filed Sep. 22, 2010", 9 pgs.

"U.S. Appl. No. 10/746,135, Response filed Mar. 30, 2009 to Non-Final Office Action mailed Sep. 30, 2008", 26 pgs.

"U.S. Appl. No. 10/746,135, Response filed Jul. 7, 2006 to Restriction Requirement mailed Jun. 9, 2006", 9 pgs.

"U.S. Appl. No. 10/746,135, Response filed Jul. 17, 2008 to Final Office Action mailed Mar. 18, 2008", 20 pgs.

"U.S. Appl. No. 10/746,135, Restriction Requirement mailed Jun. 9, 2006", 5 pgs.

"U.S. Appl. No. 10/746,844, Advisory Action mailed Oct. 31, 2008", 3 pgs.

"U.S. Appl. No. 10/746,844, Final Office Action mailed Aug. 13, 2008", 8 pgs.

"U.S. Appl. No. 10/746,844, Final Office Action mailed Aug. 17, 2009", 9 pgs.

"U.S. Appl. No. 10/746,844, Non-Final Office Action mailed Jan. 31, 2008", 8 pgs.

"U.S. Appl. No. 10/746,844, Non-Final Office Action mailed Feb. 10, 2009", 9 pgs.

"U.S. Appl. No. 10/746,844, Notice of Allowance mailed Dec. 18, 2009", 5 pgs.

"U.S. Appl. No. 10/746,844, Response filed Apr. 30, 2008 to Non-Final Office Action mailed Jan. 31, 2008", 14 pgs.

"U.S. Appl. No. 10/746,844, Response filed May 11, 2009 to Non Final Office Action mailed Feb. 10, 2009", 20 pgs.

"U.S. Appl. No. 10/746,844, Response filed Oct. 14, 2008 to Final Office Action mailed Aug. 13, 2008", 15 pgs.

"U.S. Appl. No. 10/746,844, Response filed Oct. 19, 2009 to Final Office Action mailed Aug. 17, 2009", 9 pgs.

"U.S. Appl. No. 10/746,844, Response filed Nov. 16, 2007 to Restriction Requirement mailed Oct. 17, 2007", 17 pgs.

"U.S. Appl. No. 10/746,844, Response filed Dec. 15, 2008 to Final Office Action mailed Aug. 13, 2008", 15 pgs.

"U.S. Appl. No. 10/746,844, Restriction Requirement mailed Oct. 17, 2007", 9 pgs.

"U.S. Appl. No. 10/746,845, Non-Final Office Action mailed Jan. 16, 2008", 10 pgs.

"U.S. Appl. No. 10/746,845, Notice of Allowance mailed Sep. 23, 2008", 4 pgs.
"U.S. Appl. No. 10/746,845, Response filed May 15, 2008 to Non-Final Office Action mailed Jan. 16, 2008", 18 pgs.
"U.S. Appl. No. 10/746,846, Final Office Action mailed Jan. 23, 2008", 18 pgs.
"U.S. Appl. No. 10/746,846, Response filed Jul. 7, 2006 to Restriction Requirement mailed Jun. 9, 2006", 13 pgs.
"U.S. Appl. No. 10/746,846, Restriction Requirement mailed Jun. 9, 2006", 7 pgs.
"U.S. Appl. No. 10/746,847, Examiner Interview Summary mailed Jun. 16, 2009", 9 pgs.
"U.S. Appl. No. 10/746,847, Final Office Action mailed Feb. 25, 2008", 10 pgs.
"U.S. Appl. No. 10/746,847, Final Office Action mailed Oct. 1, 2009", 10 pgs.
"U.S. Appl. No. 10/746,847, Non-Final Office Action mailed Sep. 30, 2008", 13 pgs.
"U.S. Appl. No. 10/746,847, Response filed Feb. 26, 2009 to Non-Final Office Action mailed Sep. 30, 2008", 10 pgs.
"U.S. Appl. No. 10/746,847, Response filed Jul. 14, 2008 to Final Office Action mailed Feb. 25, 2008", 11 pgs.
"U.S. Appl. No. 10/746,861, Advisory Action mailed Jul. 18, 2008", 3 pgs.
"U.S. Appl. No. 10/746,861, Advisory Action mailed Nov. 12, 2010", 3 pgs.
"U.S. Appl. No. 10/746,861, Decision on Pre-Appeal Brief mailed Nov. 21, 2008", 2 pgs.
"U.S. Appl. No. 10/746,861, Examiner Interview Summary mailed Mar. 26, 2010", 3 pgs.
"U.S. Appl. No. 10/746,861, Final Office Action mailed Apr. 21, 2008", 13 pgs.
"U.S. Appl. No. 10/746,861, Final Office Action mailed Jul. 7, 2010", 12 pgs.
"U.S. Appl. No. 10/746,861, Non-Final Office Action mailed Feb. 2, 2009", 9 pgs.
"U.S. Appl. No. 10/746,861, Non-Final Office Action mailed Nov. 24, 2009", 8 pgs.
"U.S. Appl. No. 10/746,861, Notice of Allowance mailed May 13, 2011", 7 pgs.
"U.S. Appl. No. 10/746,861, Pre-Appeal Brief Request filed Oct. 21, 2008", 5 pgs.
"U.S. Appl. No. 10/746,861, Response filed Mar. 24, 2010 to Non-Final Office Action mailed Nov. 24, 2009", 14 pgs.
"U.S. Appl. No. 10/746,861, Response filed Jul. 1, 2009 to Non-Final Office Action mailed Feb. 2, 2009", 9 pgs.
"U.S. Appl. No. 10/746,861, Response filed Sep. 7, 2010 to Final Office Action mailed Jul. 7, 2010", 13 pgs.
"U.S. Appl. No. 10/746,861, Response filed Jun. 23, 2008 to Final Office Action mailed Apr. 21, 2008", 12 pgs.
"U.S. Appl. No. 10/939,544, Examiner Interview Summary mailed Sep. 3, 2008", 14 pgs.
"U.S. Appl. No. 10/939,544, Examiner Interview Summary mailed Nov. 6, 2006", 2 pgs.
"U.S. Appl. No. 10/939,544, Final Office Action mailed Mar. 5, 2009", 14 pgs.
"U.S. Appl. No. 10/939,544, Non-Final Office Action mailed May 12, 2008", 14 pgs.
"U.S. Appl. No. 10/939,544, Notice of Allowance mailed Sep. 3, 2009", 12 pgs.
"U.S. Appl. No. 10/939,544, Response filed Feb. 12, 2008 to Non-Final Office Action mailed Oct. 12, 2007", 17 pgs.
"U.S. Appl. No. 10/939,544, Response filed Aug. 5, 2009 to Final Office Action mailed Mar. 5, 2009", 16 pgs.
"U.S. Appl. No. 10/939,544, Response filed Sep. 3, 2008 to Non-Final Office Action mailed May 12, 2008", 17 pgs.
"U.S. Appl. No. 11/078,460, Final Office Action mailed Jul. 30, 2008", 7 pgs.
"U.S. Appl. No. 11/078,460, Notice of Allowance mailed May 1, 2009", 4 pgs.
"U.S. Appl. No. 11/078,460, Notice of Allowance mailed Nov. 10, 2008", 6 pgs.
"U.S. Appl. No. 11/078,460, Response filed Apr. 18, 2008 to Non-Final Office Action mailed Jan. 18, 2008", 14 pgs.
"U.S. Appl. No. 11/078,460, Response filed Sep. 29, 2008 to Final Office Action mailed Jul. 30, 2008", 11 pgs.
"U.S. Appl. No. 11/078,460, Non-Final Office Action mailed Jan. 18, 2008", 6 pgs.
"U.S. Appl. No. 11/126,097, Final Office Action mailed Feb. 18, 2009", 10 pgs.
"U.S. Appl. No. 11/126,097, Notice of Allowance mailed Dec. 7, 2009", 7 pgs.
"U.S. Appl. No. 11/126,097, Response filed Apr. 18, 2008 to Restriction Requirement mailed Mar. 26, 2008", 13 pgs.
"U.S. Appl. No. 11/126,097, Response filed Nov. 19, 2008 to Non-Final Office Action mailed Aug. 19, 2008", 11 pgs.
"U.S. Appl. No. 11/126,097, Response filed May 4, 2009 to Final Office Action mailed Feb. 18, 2009", 11 pgs.
"U.S. Appl. No. 11/126,097, Response filed Jun. 15, 2009 to Restriction Requirement mailed May 14, 2009", 8 pgs.
"U.S. Appl. No. 11/126,097, Restriction Requirement mailed May 14, 2009", 7 pgs.
"U.S. Appl. No. 11/267,107, Final Office Action mailed Jun. 15, 2011", 8 pgs.
"U.S. Appl. No. 11/276,107, Final Office Action mailed Jan. 27, 2010", 9 pgs.
"U.S. Appl. No. 11/276,107, Non Final Office Action mailed Jun. 21, 2010", 8 pgs.
"U.S. Appl. No. 11/276,107, Non-Final Office Action mailed Jun. 26, 2009", 30 pgs.
"U.S. Appl. No. 11/276,107, Response filed Mar. 23, 2009 to Restriction Requirement mailed Feb. 20, 2009", 9 pgs.
"U.S. Appl. No. 11/276,107, Response filed Apr. 26, 2010 to Final Office Action mailed Jan. 27, 2010", 10 pgs.
"U.S. Appl. No. 11/276,107, Response filed Sep. 7, 2010 to Non-Final Office Action mailed Jun. 21, 2010", 11 pgs.
"U.S. Appl. No. 11/276,107, Response filed Sep. 28, 2009 to Non-Final Office Action mailed Jun. 26, 2009", 10 pgs.
"U.S. Appl. No. 11/276,107, Response filed Nov. 26, 2008 to Restriction Requirement mailed Oct. 31, 2008", 10 pgs.
"U.S. Appl. No. 11/276,107, Restriction Requirement mailed Oct. 31, 2008", 5 pgs.
"U.S. Appl. No. 11/276,107, Restriction Requirement mailed Feb. 20, 2009", 6 pgs.
"U.S. Appl. No. 11/312,178, Non-Final Office Action mailed May 14, 2008", 6 pgs.
"U.S. Appl. No. 11/312,178, Notice of Allowance mailed Apr. 3, 2009", 6 pgs.
"U.S. Appl. No. 11/312,178, Notice of Allowance mailed Nov. 14, 2008", 6 pgs.
"U.S. Appl. No. 11/312,178, Response filed Aug. 14, 2008 to Non-Final Office Action mailed May 14, 2008", 14 pgs.
"U.S. Appl. No. 11/482,357, Non-Final Office Action mailed Jul. 17, 2009", 12 pgs.
"U.S. Appl. No. 11/482,357, Notice of Allowance mailed Mar. 25, 2010", 4 pgs.
"U.S. Appl. No. 11/482,357, Preliminary Statement mailed Oct. 30, 2006", 3 pgs.
"U.S. Appl. No. 11/482,357, Response filed Dec. 17, 2009 to Non-Final Office Action mailed Jul. 17, 2009", 13 pgs.
"U.S. Appl. No. 11/558,083, 1.312 Amendment filed Jul. 8, 2010", 10 pgs.
"U.S. Appl. No. 11/558,083, Non-Final Office Action mailed Jun. 26, 2009", 17 pgs.
"U.S. Appl. No. 11/558,083, Preliminary Amendment mailed Nov. 13, 2006", 3 pgs.
"U.S. Appl. No. 11/558,083, Response to 312 Amendment mailed Jul. 21, 2010", 2 pgs.
"U.S. Appl. No. 11/558,083, Response filed Dec. 22, 2009 to Non-Final Office Action mailed Jun. 26, 2009", 15 pgs.
"U.S. Appl. No. 11/621,194, Final Office Action mailed May 19, 2010", 8 pgs.
"U.S. Appl. No. 11/621,194, Non-Final Office Action mailed Oct. 1, 2009", 22 pgs.

"U.S. Appl. No. 11/621,194, Response filed Aug. 19, 2010 to Final Office Action mailed May 19, 2010", 8 pgs.
"U.S. Appl. No. 11/933,252, Preliminary Statement filed Oct. 31, 2007", 3 pgs.
"U.S. Appl. No. 11/933,268, Preliminary Statement filed Oct. 31, 2007", 2 pgs.
"U.S. Appl. No. 12/126,182, Non-Final Office Action mailed Jul. 23, 2010", 9 pgs.
"U.S. Appl. No. 12/126,182, Notice of Allowance mailed Apr. 18, 2011", 12 pgs.
"U.S. Appl. No. 12/126,182, Response filed Oct. 25, 2010 to Non-Final Office Action mailed Jul. 23, 2010", 12 pgs.
"U.S. Appl. No. 12/257,079, Final Office Action mailed May 10, 2011", 11 pgs.
"U.S. Appl. No. 12/257,079, Non-Final Office Action mailed Oct. 1, 2010", 10 pgs.
"U.S. Appl. No. 12/257,079, Response filed Mar. 1, 2011 to Non-Final Office Action mailed Oct. 1, 2010", 9 pgs.
"U.S. Appl. No. 12/257,079, Response filed Sep. 7, 2010 to Restriction Requirement mailed Aug. 5, 2010", 9 pgs.
"U.S. Appl. No. 12/257,079, Response filed Aug. 10, 2011 to Final Office Action mailed May 10, 2011", 9 pgs.
"U.S. Appl. No. 12/257,079, Restriction Requirement mailed Jun. 5, 2010", 5 pgs.
"U.S. Appl. No. 12/257,079, Restriction Requirement mailed Aug. 5, 2010", 5 pgs.
"U.S. Appl. No. 12/321,949, Final Office Action mailed Dec. 16, 2010", 8 pgs.
"U.S. Appl. No. 12/321,949, Non-Final Office Action mailed Jul. 29, 2010", 8 pgs.
"U.S. Appl. No. 12/321,949, Response filed Mar. 9, 2011 to Final Office Action mailed Dec. 16, 2010", 8 pgs.
"U.S. Appl. No. 12/321,949, Response filed Jun. 3, 2010 to Restriction Requirement mailed May 3, 2010", 11 pgs.
"U.S. Appl. No. 12/321,949, Response filed Oct. 29, 2010 to Non-Final Office Action mailed Jul. 29, 2010", 9 pgs.
"U.S. Appl. No. 12/321,949, Restriction Requirement mailed May 3, 2010", 7 pgs.
"U.S. Appl. No. 12/368,842, Final Office Action mailed Jul. 19, 2011", 13 pgs.
"U.S. Appl. No. 12/368,842, Non Final Office Action mailed Dec. 28, 2010", 10 pgs.
"U.S. Appl. No. 12/368,842, Response filed Nov. 1, 2010 to Restriction Requirement mailed Sep. 30, 2010", 9 pgs.
"U.S. Appl. No. 12/368,842, Response filed Mar. 28, 2011 to Non-Final Office Action mailed Dec. 28, 2010", 10 pgs.
"U.S. Appl. No. 12/368,842, Restriction Requirement mailed Sep. 30, 2010", 6 pgs.
"U.S. Appl. No. 12/543,654, Non-Final Office Action mailed Jul. 11, 2011", 6 pgs.
"U.S. Appl. No. 12/627,562, Non-Final Office Action mailed Jun. 15, 2011", 10 pgs.
"U.S. Appl. No. 12/693,660, Final Office Action mailed Apr. 21, 2011", 10 pgs.
"U.S. Appl. No. 12/693,660, Non-Final Office Action mailed Oct. 28, 2010", 8 pgs.
"U.S. Appl. No. 12/693,660, Response filed Feb. 28, 2011 to Non-Final Office Action mailed Oct. 28, 2010", 9 pgs.
"U.S. Appl. No. 12/693,660, Response filed Sep. 2, 2010 to Restriction Requirement mailed Aug. 2, 2010", 7 pgs.
"U.S. Appl. No. 12/693,660, Restriction Requirement mailed Aug. 2, 2010", 8 pgs.
"U.S. Appl. No. 12/749,939, Non-Final Office Action with Restriction Requirement mailed Mar. 21, 2011", 14 pgs.
"U.S. Appl. No. 12/749,939, Response filed Aug. 22, 2011 to Non-Final Office Action mailed Mar. 21, 2011", 13 pgs.
"European Application Serial No. 05787559.3, Response filed Jul. 23, 2009 to Communication mailed Jan. 29, 2009", 12 pgs.
"European Application Serial No. 06827323.4, Communication mailed Jun. 2, 2009", 2 pgs.
"European Application Serial No. 06827323.4, Communication mailed Nov. 12, 2008", 3 pgs.
"European Application Serial No. 06827323.4, Response filed Apr. 24, 2009 to Communication mailed Nov. 12, 2008", 6 pgs.
"European Application Serial No. 06827323.4, Summons to Attend Oral Proceedings mailed May 19, 2010", 3 pgs.
"European Application Serial No. 06827323.4, Written Submissions filed Sep. 23, 2010", 4 pgs.
"European Application Serial No. 07861710.7, Office Action mailed Aug. 23, 2010", 3 pgs.
"European Application Serial No. 07861710.7, Response filed Feb. 28, 2011 to Non Final Office Action mailed Aug. 23, 2010", 15 pgs.
"European Application Serial No. 5787559.3, Office Action mailed Jan. 29, 2009", 10 pgs.
"International Application Serial No. PCT/US2004/036606, Written Opinion dated Mar. 10, 2005", 5 pgs.
"International Application Serial No. PCT/US2004/043691, International Search Report mailed Mar. 22, 2005", 3 pgs.
"International Application Serial No. PCT/US2004/043691, Written Opinion mailed Mar. 22, 2005", 7 pgs.
"International Application Serial No. PCT/US2007/023288, International Search Report and Written Opinion mailed Apr. 23, 2008", 13 pgs.
"Japanese Application Serial No. 2006-547356, Notice of Allowance mailed May 18, 2011", 3 pgs.
"Japanese Application Serial No. 2006-547356, Office Action mailed Jul. 6, 2010", w/ English translation, 7 pgs.
"Japanese Application Serial No. 2006-547356, Office Action Response filed Oct. 5, 2010", (w/ English Translation of Amended Claims), 68 pgs.
"Japanese Application Serial No. 2006-547356, Response filed Apr. 20, 2011 to Office Action mailed Feb. 1, 2011", 11 pgs.
"Japanese Application Serial No. 2006-547356, Office Action mailed Feb. 1, 2011", (w/ English Translation), 15 pgs.
"Japanese Application Serial No. 2006-547492, Notice of Allowance dated Oct. 29, 2010", (w/ English Translation), 2 pgs.
"Japanese Application Serial No. 2006-547492, Office Action mailed Jun. 8, 2010", (w/ English Translation), 5 pgs.
"Japanese Application Serial No. 2006-547492, Response filed Oct. 6, 2010 to Office Action mailed Jun. 8, 2010", (w/ English Translation of Amended Claims), 14 pgs.
"Japanese Application Serial No. 2007-531174, Office Action mailed Apr. 28, 2011", 3 pgs.
Kramer, Andrew P., et al., "U.S. Appl. No. 12/840,981, Application filed Jul. 21, 2010", 77 pgs.
Leutmezer, F, et al., "Electrocardiographic Changes at the onset of Epileptic Seizures", Epilepsia, 44(3), (2003), 348-354.
Libbus, I., et al., "Hypertension Therapy Based on Activity and Circadian Rhythm", U.S. Appl. No. 12/968,797, filed Dec. 15, 2010, 75 pgs.
Libbus, I., "Implantable Systems and Devices for Providing Cardiac Defibrillation and Apnea Therapy", U.S. Appl. No. 13/198,477, filed Aug. 4, 2011, 70 pgs.
Libbus, Imad, "Baroreflex Activation Therapy with Conditional Shut Off U.S. Appl. No. 12/783,119", Application filed May 19, 2010, 94 pgs.
McMahon, N. C., et al., "Reflex responses from the main pulmonary artery and bifurcation in anaesthetised dogs.", Experimental Physiology, 85(4), (2000), 411-420.
Pauza, D. H., et al., "Morphology, distribution, and variability of the epicardiac neural ganglionated subplexuses in the human heart", The Anat. Rec. 259(4), (2000), 353-382.
Rugg-Gunn, F. J, et al., "Cardiac arrhythmias in focal epilepsy: a prospective long-term study.", Lancet, 364(9452), (Dec. 18-31, 2004), 2212-9.

* cited by examiner

US 8,126,560 B2

STIMULATION LEAD FOR STIMULATING THE BARORECEPTORS IN THE PULMONARY ARTERY

CROSS REFERENCE TO RELATED APPLICATIONS

The following commonly assigned U.S. patent applications are related, are all filed on the same date as the present application and are all herein incorporated by reference in their entirety: "Baroreflex Stimulation System to Reduce Hypertension," Ser. No. 10/746,134; and "Lead for Stimulating the Baroreceptors in the Pulmonary Artery," Ser. No. 10/746,861.

FIELD

This application relates generally to implantable medical devices and, more particularly, to systems, devices and methods for reducing hypertension using baroreceptor stimulation.

BACKGROUND

Medical leads have a distal end having one or more electrodes and a proximal end having a terminal that is coupled to a pulse generator. Electrical therapy is delivered from the pulse generator to the body via the electrode.

Hypertension is a cause of heart disease and other related cardiac co-morbidities. Hypertension occurs when blood vessels constrict. As a result, the heart works harder to maintain flow at a higher blood pressure, which can contribute to heart failure. Many patients who suffer from hypertension do not respond to treatment, such as treatments related to lifestyle changes and hypertension drugs.

A pressoreceptive region is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activate baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance.

The general concept of stimulating afferent nerve trunks leading from baroreceptors is known. For example, direct electrical stimulation has been applied to the vagal nerve and carotid sinus using nerve cuffs. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension.

What is needed is a less invasive technique for providing long-term electrical stimulation of the baroreflex.

SUMMARY

One aspect provides a lead for placement in the pulmonary artery. The lead includes a flexible lead body extending from a proximal end to a distal end, the distal end having a biased portion having an outer diameter dimensioned to abut a wall of a pulmonary artery, an electrode coupled proximate the distal end. An implantable pulse generator is electrically coupled to the electrode. The implantable pulse generator is adapted to deliver a baroreflex stimulation signal to a baroreceptor in the pulmonary artery via the electrode.

One aspect includes a method. The method includes positioning an electrode on a distal end of a lead within a pulmonary artery, the distal end having a biased portion such that an outer diameter of the biased portion abuts a wall of the pulmonary artery, and delivering a baroreflex stimulation signal to a baroreceptor in the pulmonary artery via the electrode.

DETAILED DESCRIPTION

Figure 1:
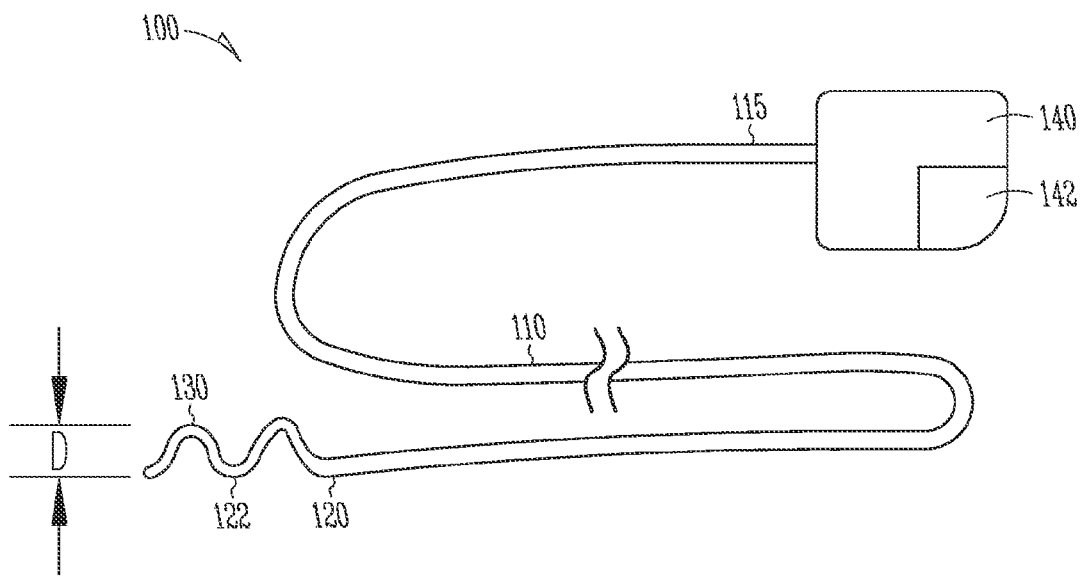
FIG. 1 shows a lead and pulse generator, in accordance with one embodiment.

The following detailed description and accompanying drawings show specific embodiments in which the present invention may be practiced. These embodiments are described in sufficient detail to enable those skilled in the art to practice the invention. Other embodiments may be utilized and structural changes may be made without departing from the scope of the present invention.

A brief discussion of hypertension and the physiology related to baroreceptors is provided to assist the reader with understanding this disclosure. This brief discussion introduces hypertension, the autonomic nervous system, and baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The subject matter of this disclosure generally refers to the effects that the ANS has on the heart rate and blood pressure, including vasodilation and vasoconstriction. The heart rate and force is increased when the sympathetic nervous system is stimulated, and is decreased when the sympathetic nervous system is inhibited (e.g. when the parasympathetic nervous system is stimulated).

Baroreflex is a reflex triggered by stimulation of a baroreceptor. A baroreceptor includes any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Additionally, a baroreceptor includes afferent nerve trunks, such as the vagus, aortic and carotid nerves, leading from the sensory nerve endings. Stimulating baroreceptors inhibits sympathetic nerve activity (stimulates the parasympathetic nervous system) and reduces systemic arterial pressure by decreasing peripheral vascular resistance. Baroreceptors are naturally stimulated by internal pressure and the stretching of the arterial wall.

Some aspects of the present subject matter locally and directly stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating baroreceptor sites in the aorta.

FIG. 1 shows a lead 100 according to one embodiment. Lead 100 includes a flexible lead body 110 extending from a proximal end 115 to a distal end 120. An electrode 130 is coupled proximate the distal end 120 of lead body 110. The distal end 120 includes a biased portion 122. Lead 100 is adapted to deliver stimulation to baroreceptors in the pulmonary artery. For example, the biased portion 122 can have a biased configuration having an outer diameter, D, dimensioned to abut a wall of a pulmonary artery to hold the electrode in place without any active fixation, as will be explained below.

Lead 100 is coupled to an implantable pulse generator 140. Lead 100 includes conductors, such as coiled conductors that electrically couple pulse generator 140 to electrode 130. Accordingly, implantable pulse generator 140 can deliver a baroreflex stimulation signal to a baroreceptor in the pulmonary artery via the electrode 130. The lead further includes outer insulation to insulate the conductor. The system can include a unipolar system with the case acting as an electrode or a bipolar system with a pulse between two distally located electrodes.

In one embodiment, pulse generator 140 includes hardware, circuitry and software to perform NS functions. Some embodiments can also perform an AHT function. Pulse generator includes controller circuitry 142. The controller circuitry 142 is capable of being implemented using hardware, software, and combinations of hardware and software. For example, according to various embodiments, the controller circuitry 142 includes a processor to perform instructions embedded in a memory to perform functions associated with NS therapy such as AHT therapy. In one example, the pulse generator delivers a pulse train having a frequency of between about 10 to 150 hertz via the electrode. In one embodiment, the pulse generator can deliver a waveform of 30 hertz, 2.5 msec, at 5 volts. Some embodiments deliver a waveform of 100 hertz, 1.0 msec, at 1, 3, or 5 volts, for example.

Figure 2:
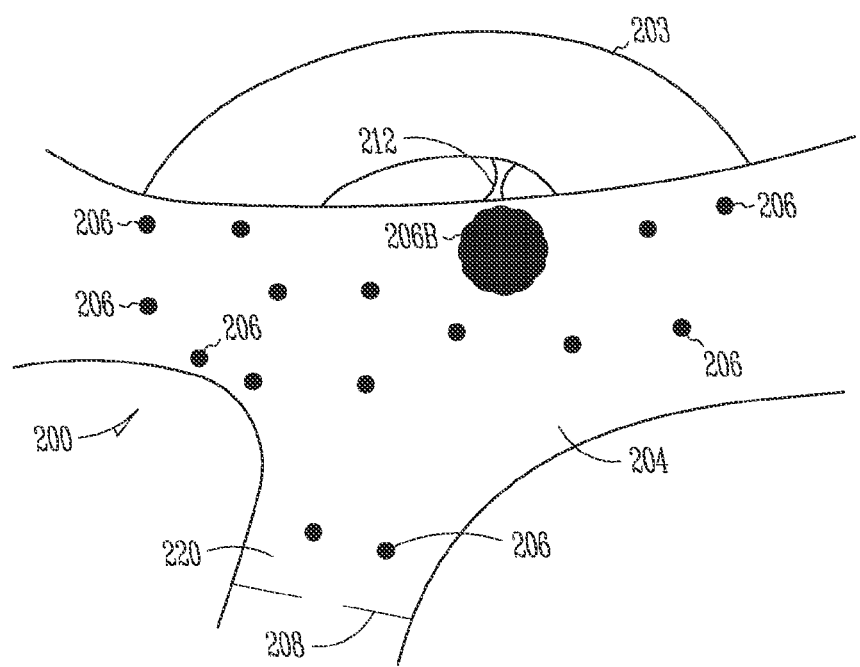
FIG. 2 shows details of a heart.

FIG. 2 shows a representation of a portion of a heart 200. Heart 200 includes an aortic arch 203 and a pulmonary artery 204. Pulmonary artery 204 includes a plurality of baroreceptors 206. A lead, such as lead 100 (FIG. 1), is capable of being intravascularly inserted through a peripheral vein and through the tricuspid valve into the right ventricle of the heart (not expressly shown in the figure) similar to a cardiac pacemaker lead, and continue from the right ventricle through the pulmonary valve 208 into the pulmonary artery 204.

A portion of the pulmonary artery 204 and aorta arch 203 are proximate to each other. According to various aspects of the present subject matter, the baroreflex is stimulated in or around the pulmonary artery by at least one electrode intravascularly inserted into the pulmonary artery. Aspects of the present subject matter provide a relatively noninvasive surgical technique to implant a baroreceptor stimulator intravascularly into the pulmonary artery. The baroreceptors 206, for example, are sensitive to stretching of the wall resulting from increased pressure from within. Activation of these nerve endings reduces pressure.

As illustrated, the pulmonary artery 204 includes a number of baroreceptors 206, as generally indicated by the dark areas. Furthermore, a cluster of closely spaced baroreceptors 206B is situated near the attachment of the ligamentum arteriosum 212. According to various embodiments of the present subject matter, a lead is inserted through a peripheral vein and threaded through the tricuspid valve into the right ventricle, and from the right ventricle through the pulmonary valve 208 and into the pulmonary artery 204 to simulate baroreceptors in and/or around the pulmonary artery. In various embodiments, for example, the lead is positioned to stimulate the cluster of baroreceptors 206B near the ligamentum arteriosum 212.

There are also baroreceptor fields in the aortic arch 203, near the ligamentum arteriosum 212, and in the trunk 220 of the pulmonary artery 204. Some embodiments position the lead in the pulmonary artery to stimulate baroreceptor sites in the aorta, possibly via the ligamentum arteriosum, or in the pulmonary trunk, or in either the right or left pulmonary arteries.

Figure 3:
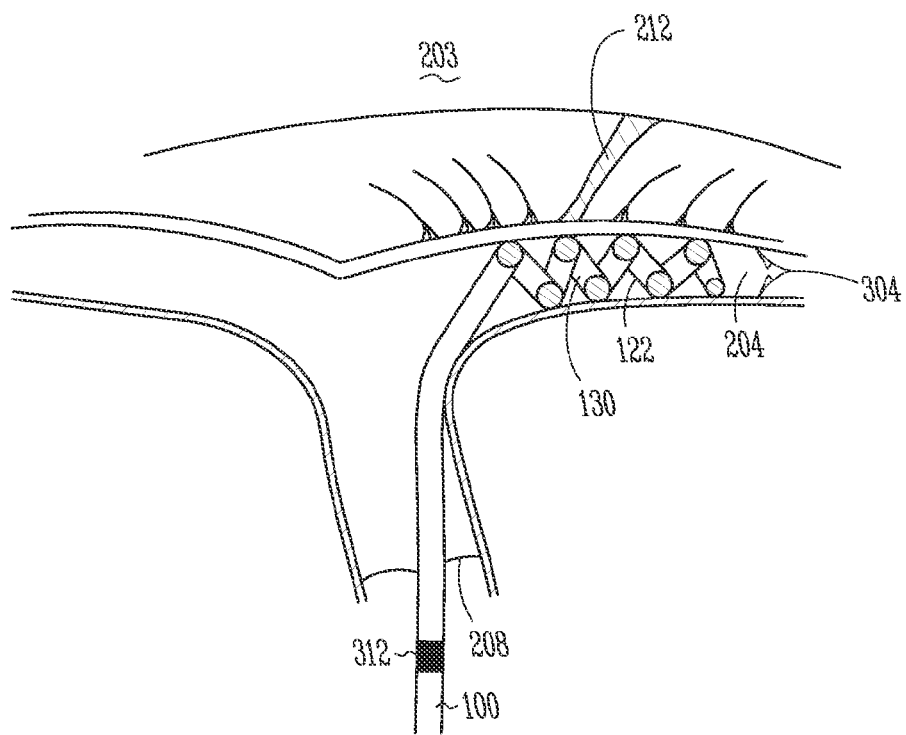
FIG. 3 shows the lead of FIG. 1 implanted in a heart, in accordance with one embodiment.

FIG. 3 shows a cross-section of electrode 130 mounted in pulmonary artery 204, in accordance with one embodiment. In one embodiment, biased portion 122 includes an elongated spiral configuration with electrode 130 being a coiled electrode that is exposed to have substantially complete annular contact with the wall surface 304 of the pulmonary artery 204. This allows for distributed stimulation along the length of the biased portion 122 and distributed wall fixation. Thus, for example, the entire electrode 130 can be an exposed electrode manufactured in a spiral configuration. As will be discussed below, some embodiments can include two or more discrete electrodes placed along the distal end of the lead. In some embodiments, portions of the surface of the electrode can be masked off to be electrically insulated.

As noted, the outer diameter of the biased portion 122 is designed to expand to abut the outer walls 304 of the pulmonary artery so as to fix the lead and the electrode in place by frictional forces. In this example, the electrode is adapted to be located near the ligamentum arteriosum 212 of the left pulmonary artery 204. In some embodiments, at least a portion of electrode 130 can include a porous surface to further help fix the electrode within the artery.

In one embodiment, the biased portion 122 can have an outer biased diameter of about 10 mm to about 20 mm. Other embodiments can have a larger diameter. One example has a pitch of at least 5 coils per inch to provide high arterial surface contact and increased fixation. In general, the distal end and the electrode are dimensioned to optimize direct, low-voltage, high-frequency nerve stimulation.

In one embodiment, lead 100 can include a second electrode 312 located proximally from electrode 130. This electrode can be used for bradyarrhythmia therapy, tachyarrhythmia therapy, as a sensing electrode, or as a cathode for electrode 130.

In one example, electrode 130 is adapted to be chronically implanted in the pulmonary artery. For example, by passively mounting the electrode within the artery, no long-term damage is done to the artery.

Figure 4:
FIG. 4 shows a lead in accordance with one embodiment.
Figure 5:
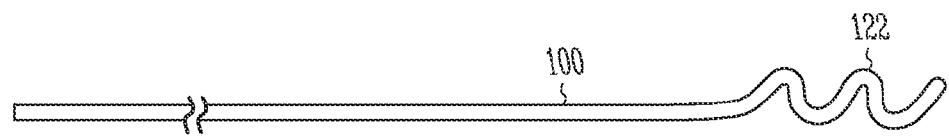
FIG. 5 shows the lead of FIG. 4 with the distal end in a biased configuration.

FIGS. 4 and 5 show lead 100, in accordance with one embodiment. Lead 100 can be implanted using a stylet 402 that is removed once the lead is positioned correctly. Removing stylet 402 from the lead allows distal end 122 to expand to its biased configuration until the electrode abuts the walls of the artery, as discussed above.

Figure 6:
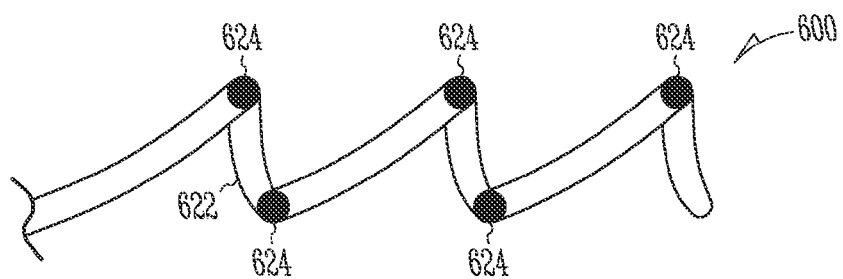
FIG. 6 shows a lead in accordance with one embodiment.

FIG. 6 shows a portion of a lead 600, in accordance with one embodiment. Lead 600 includes a biased distal portion 622, similar to biased portion 122 discussed above. In this embodiment, the biased portion 622 includes two or more discrete electrodes 624 exposed on the outer surface and outer diameter of the biased portion. In one embodiment, these discrete electrodes allow localized, but distributed stimulation when implanted in an artery. Alternatively, some of the discrete electrodes 624 can be coupled to a separate conductor of lead 600. In this example, the user implants the electrode and then tests each electrode separately to discover which gives the best baroreflex response. Then, the non-productive electrode or electrodes can be turned off, or used only for sensing, or other purposes. In some embodiments, discrete electrodes 624 can be porous to provide further fixation within the artery.

Figure 7:
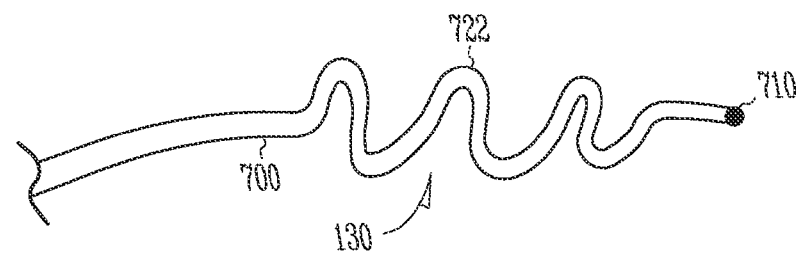
FIG. 7 shows a side view of a lead in accordance with one embodiment.

FIG. 7 illustrates a baroreceptor stimulation lead 700 with an integrated pressure sensor 710 (IPS), according to various embodiments of the present subject matter. Lead 700 can include an IPS 710 with a baroreceptor stimulator electrode to monitor changes in blood pressure, and thus to monitor the effect of the baroreceptor stimulation. In various embodiments, micro-electrical mechanical systems (MEMS) technology can be used to sense the blood pressure. Some sensor embodiments determine blood pressure based on a displacement of a membrane.

In one example use of lead 700, a system can include baroreceptor stimulation circuitry and sensor circuitry. The circuitry can be within pulse generator 140 (FIG. 1) or be a separate system communicating wirelessly with the pulse generator. One or more leads can be connected to the sensor circuitry and baroreceptor stimulation circuitry. The baroreceptor stimulation circuitry is used to apply electrical stimulation pulses to desired baroreceptors sites, such as baroreceptor sites in the pulmonary artery, through one or more stimulation electrodes, such as electrode 130 on biased portion 722. The sensor circuitry is used to detect and process ANS nerve activity and/or surrogate parameters such as blood pressure, respiration and the like, to determine the ANS activity.

Lead 700, for example, is capable of being intravascularly introduced to stimulate a baroreceptor site, such as the baroreceptor sites in the pulmonary artery, aortic arch, or ligamentum arteriosum. One or more additional electrodes can be provided to pace and/or sense cardiac activity, such as that which may occur within the right ventricle with the sensor 710 located in or near the pulmonary artery and programmed to stimulate and sense, either directly or indirectly through surrogate parameters, baroreflex activity.

Figure 8:
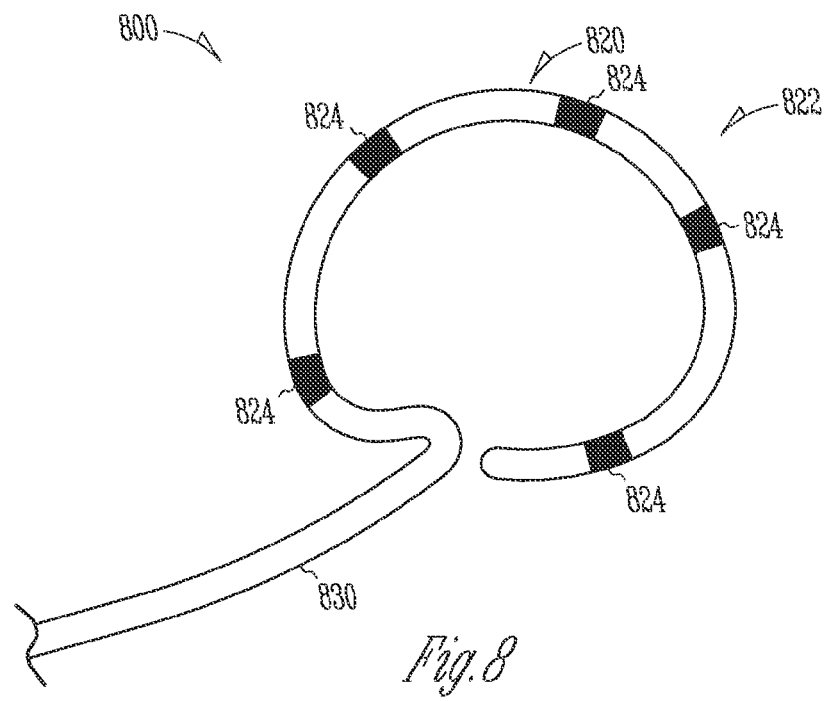
FIG. 8 shows a portion of a lead in accordance with one embodiment.

FIG. 8 shows a lead 800 according to one embodiment, lead 800 includes a distal portion 820 including a biased circular portion 822. In this embodiment, a plurality of discrete electrodes 824 are placed around the outer circumference of the circular portion 822. In other embodiments, the entire biased circular portion can be an exposed electrode. Circular biased portion 822 is dimensioned to fixate the distal end 820 within the pulmonary artery. For example, the biased circular portion can have an outer diameter of between 10 mm and 20 mm. In one embodiment, the circular plane of the distal portion 820 of the lead 800 is perpendicular to the long axis 830 of the lead body (i.e. shaped like a lasso). A distal end fashioned in this way tends to stimulate the pulmonary artery in a plane or cross section of the artery. Other embodiments can use other angles as needed.

To provide hypertension therapy according to one embodiment, a lead, such as any of the leads discussed herein, is intravascularly inserted through a peripheral vein and through the tricuspid valve into the right ventricle of the heart and then from the right ventricle through the pulmonary valve into the pulmonary artery. An electrode on the lead is fixated to a region of the pulmonary artery having one or more baroreceptors. One example passively fixates the electrode proximate the ligamentum arteriosum of the left pulmonary artery. In one embodiment, the pulse generator designed to intermittently pace with low-voltage, high frequency pulse train. For example, one embodiment delivers at least a 10 hertz pulse train via the electrode. As noted above, in some embodiments the pulse generator can deliver a waveform of 30 hertz, 2.5 msec, at 5 volts. Some embodiments deliver a waveform of 100 hertz, 1.0 msec, at 1, 3, or 5 volts, for example. In some embodiments, the baroreceptor can be intermittently paced for about 5 to 10 seconds each minute at a voltage of about 0.1 volts to 10 volts and a frequency between about 10 Hz and 150 Hz. Some examples utilize a voltage between about 1 volt to about 10 volts.

The leads of the present subject matter are easy to implant and deliver uncomplicated waveforms. Moreover, the baroreceptor pacing response is immediate and reversible.

Further embodiments can include a sensor to monitor blood pressure. The sensor can sense a physiological parameter regarding an efficacy of the baroreflex therapy and provides a signal indicative of the efficacy of the baroreflex therapy. For example, a controller can be connected to a pulse generator to control the baroreflex stimulation signal and to the sensor to receive the signal indicative of the efficacy of the baroreflex therapy. In some examples, the pulse generator can be further adapted to generate a cardiac pacing signal, and the lead can include a second electrode to be positioned to deliver the cardiac pacing signal to capture the heart. The present lead allows for chronic indwelling and is easy to implant.

In various embodiments of baroreceptor pacing according to the present subject matter, the system can deliver the pulse train intermittently with no sensing, or the system can be activated by the user when the user is at rest, or it can be activated by a timer to be periodically turned off and on, or it can be activated when the user goes to sleep, for example.

According to various embodiments, the stimulator circuitry of the pulse generator can include one or more functions as described in the commonly assigned U.S. patent application filed on the same date as the present application and incorporated by reference in its entirety: "Baroreflex Stimulation System to Reduce Hypertension," Ser. No. 10/746,134, filed on Dec. 24, 2003.

For example, various embodiments of the present subject matter relate to baroreflex stimulator systems. Such baroreflex stimulation systems are also referred to herein as neural stimulator (NS) devices or components. Examples of neural stimulators include anti-hypertension (AHT) devices or AHT components that are used to treat hypertension. Various embodiments of the present subject matter include stand-alone implantable baroreceptor stimulator systems, include implantable devices that have integrated NS and cardiac rhythm management (CRM) components, and include systems with at least one implantable NS device and an implantable CRM device capable of communicating with each other either wirelessly or through a wire lead connecting the implantable devices. Integrating NS and CRM functions that are either performed in the same or separate devices improves aspects of the NS therapy and cardiac therapy by allowing these therapies to work together intelligently.

Thus, various embodiments of the present subject matter provide an implantable NS device that automatically modulates baroreceptor stimulation using an IPS. Integrating the pressure sensor into the lead provides localized feedback for the stimulation. This localized sensing improves feedback control. For example, the integrated sensor can be used to compensate for inertia of the baroreflex such that the target is not continuously overshot. According to various embodiments, the device monitors pressure parameters such as mean arterial pressure, systolic pressure, diastolic pressure and the like. As mean arterial pressure increases or remains above a programmable target pressure, for example, the device stimulates baroreceptors at an increased rate to reduce blood pressure and control hypertension.

As mean arterial pressure decreases towards the target pressure, the device responds by reducing baroreceptor stimulation. In various embodiments, the algorithm takes into account the current metabolic state (cardiac demand) and adjusts neural stimulation accordingly. A NS device having an IPS is able to automatically modulate baroreceptor stimulation, which allows an implantable NS device to determine the level of hypertension in the patient and respond by delivering the appropriate level of therapy. However, it is noted that other sensors, including sensors that do not reside in an NS or neural stimulator device, can be used to provide close loop feedback control.

An aspect of the present subject matter relates to a chronically-implanted stimulation system specially designed to treat hypertension by monitoring blood pressure and stimulating baroreceptors to activate the baroreceptor reflex and inhibit sympathetic discharge from the vasomotor center. Baroreceptors are located in various anatomical locations such as the carotid sinus and the aortic arch. Other baroreceptor locations include the pulmonary artery, including the ligamentum arteriosum, and sites in the atrial and ventricular chambers. In various embodiments, the system is integrated into a pacemaker/defibrillator or other electrical stimulator system. Components of the system include a high-frequency pulse generator, sensors to monitor blood pressure or other pertinent physiological parameters, leads to apply electrical stimulation to baroreceptors, algorithms to determine the appropriate time to administer stimulation, and algorithms to manipulate data for display and patient management.

Various embodiments relates to a system that seeks to deliver electrically mediated NS therapy, such as AHT therapy, to patients. Various embodiments combine a "stand-alone" pulse generator with a minimally invasive, unipolar lead that directly stimulates baroreceptors in the vicinity of the heart, such as in the pulmonary artery. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, etc.) so as to maintain a desired quality of life. In various embodiments, an implanted system includes a pulse generating device and lead system, the stimulating electrode of which is positioned near endocardial baroreceptor tissues using transvenous implant technique(s).

Another embodiment includes a system that combines NS therapy with traditional bradyarrhythmia, tachyarrhythmia, and/or congestive heart failure (CHF) therapies. Some embodiments use an additional "baroreceptor lead" that emerges from the device header and is paced from a modified traditional pulse generating system. In another embodiment, a traditional CRM lead is modified to incorporate proximal electrodes that are naturally positioned near baroreceptor sites. With these leads, distal electrodes provide CRM therapy and proximal electrodes stimulate baroreceptors.

Figure 9:
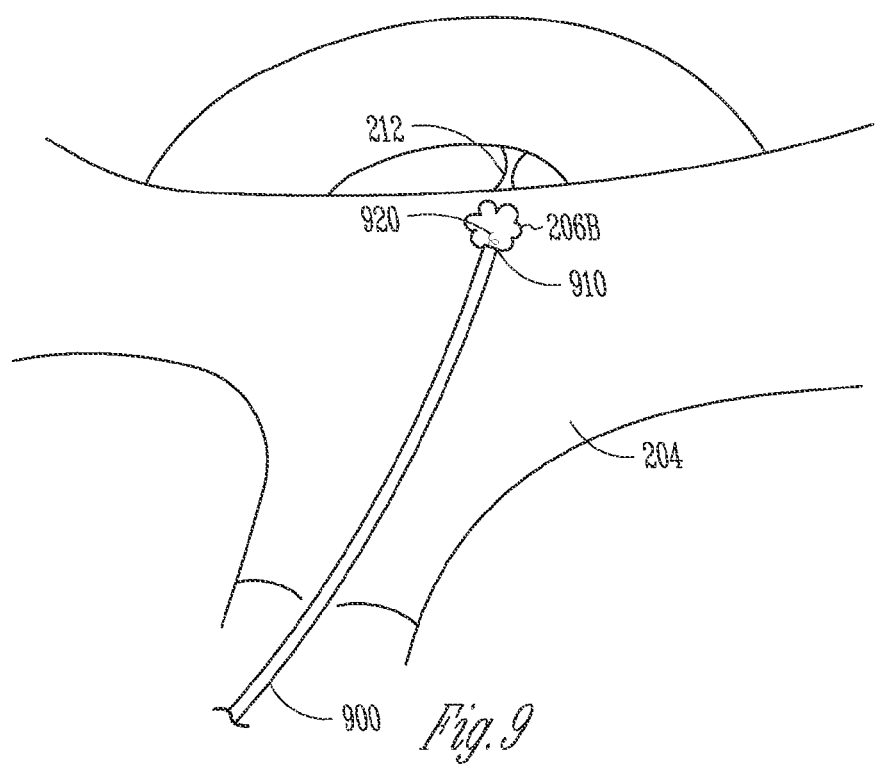
FIG. 9 shows a lead implanted in accordance with one embodiment.

For example, FIG. 9 schematically shows an unbiased lead 900 having an electrode 910 on a distal end and an active or positive fixation mechanism, such as a helix 920. Electrode 910 is intended to be implanted at or near a site of high baroreceptor concentration, such as baroreceptor site 206B in the pulmonary artery 204. At implant, lead 900 would be passed through the heart and into the pulmonary artery. With the distal end of lead 900 generally straight (unbiased), the act of implantation would naturally position the distal electrode end 910 at or near baroreceptor site 206B. Stimulation at the 206B location by a single electrode can be preferable, in some instances, to advancing a longer lead device deeper into the pulmonary artery to attempt stimulation of a number of diffuse locations.

Various embodiments of the present subject matter relate to a method of sensing atrial activation and confining pulmonary artery stimulation to the atrial refractory period, preventing unintentional stimulation of nearby atrial tissue. An implantable baroreceptor stimulation device monitors atrial activation with an atrial sensing lead. A lead in the pulmonary artery stimulates baroreceptors in the vessel wall. However, instead of stimulating these baroreceptors continuously, the stimulation of baroreceptors in the pulmonary artery occurs during the atrial refractory period to avoid capturing nearby atrial myocardium, maintaining the intrinsic atrial rate and activation. Various embodiments of the present subject matter combine an implantable device for stimulating baroreceptors in the wall of the pulmonary artery with the capability for atrial sensing. Various embodiments stimulate baroreceptors in the cardiac fat pads, in the heart chambers, and/or afferent nerves.

For example, the pulse generator can include a transceiver and associated circuitry for use to communicate with a programmer or another external or internal device. Various embodiments have wireless communication capabilities. For example, some transceiver embodiments use a telemetry coil to wirelessly communicate with a programmer or another external or internal device.

The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An apparatus comprising:
a flexible lead body extending from a proximal end to a distal end, the distal end having a biased portion having an outer diameter dimensioned to abut a wall of a pulmonary artery;
an electrode coupled proximate the distal end; and
an implantable pulse generator electrically coupled to the electrode, wherein the implantable pulse generator is programmed to deliver a baroreflex stimulation signal to a baroreceptor in the pulmonary artery via the electrode such that the stimulation signal causes a lowering of blood pressure, wherein the implantable pulse generator is programmed such that the signal is delivered for about 5 seconds to about 10 seconds each minute at a voltage of about 0.1 volts to about 10 volts and a frequency of about 10 Hz to 150 Hz.

2. The apparatus of claim 1, wherein the biased portion has an outer diameter between about 10 mm and about 20 mm.

3. The apparatus of claim 1, wherein the biased portion is adapted to fix the lead in place by frictional forces.

4. The apparatus of claim 1, wherein the biased portion includes a spiral configuration.

5. The apparatus of claim 1, wherein the electrode includes a porous surface.

6. The apparatus of claim 1, wherein the lead includes two or more discrete electrodes located on the biased portion of the lead.

7. The apparatus of claim 1, wherein the lead includes a second electrode located proximally from the distal end.

8. The apparatus of claim 1, wherein the signal is at a voltage of about 1 V to about 10 V.

9. The apparatus of claim 1, wherein the electrode is adapted to be chronically implanted in the pulmonary artery.

10. The apparatus of claim 1, wherein the lead further includes a sensor to monitor blood pressure.

11. The apparatus of claim 1, wherein the electrode is adapted to be located near the ligamentum arteriosum of the left pulmonary artery.

12. The apparatus of claim 1, further including a sensor to sense a physiological parameter regarding an efficacy of the baroreflex therapy and to provide a signal indicative of the efficacy of the baroreflex therapy.

13. The apparatus of claim 12, further including a controller connected to the pulse generator to control the baroreflex stimulation signal and to the sensor to receive the signal indicative of the efficacy of the baroreflex therapy.

14. The apparatus of claim 1, wherein the lead is adapted to be fed through a right ventricle and a pulmonary valve into the pulmonary artery to position the electrode in the pulmonary artery.

15. The apparatus of claim 1, wherein the pulse generator is further adapted to generate a cardiac pacing signal, the lead further including a second electrode to be positioned to deliver the cardiac pacing signal to capture the heart.

16. The apparatus of claim 1, wherein the implantable pulse generator is programmed to deliver the baroreflex stimulation signal to the baroreceptor such that the stimulation signal causes a lowering of blood pressure.

17. An apparatus comprising:
a flexible lead body extending from a proximal end to a distal end;
an electrode coupled to the distal end of the lead body; and
an implantable pulse generator electrically coupled to the electrode, the implantable pulse generator being programmed to deliver a baroreflex stimulation signal to a baroreceptor in the pulmonary artery via the electrode;
wherein a biased portion of the distal end is adapted to passively fixate the electrode within the pulmonary artery;
wherein the implantable pulse generator is programmed to deliver the baroreflex stimulation signal to the baroreceptor such that the stimulation signal causes a lowering of blood pressure, wherein implantable pulse generator is programmed such that the signal is delivered for about 5 seconds to about 10 seconds each minute at a voltage of about 0.1 volts to about 10 volts and a frequency of about 10 Hz to 150 Hz.

18. The apparatus of claim 17, wherein the biased portion includes a spiral structure.

19. The apparatus of claim 17, wherein the biased portion includes a circular structure.

20. The apparatus of claim 17, wherein the biased portion includes an outer diameter between about 10 mm to about 20 mm.

21. The apparatus of claim 17, wherein the signal is at a voltage of about 1 V to about 10 V.

22. The apparatus of claim 17, wherein the implantable pulse generator is programmed to deliver the baroreflex stimulation signal to the baroreceptor such that the stimulation signal causes a lowering of blood pressure.

23. A method comprising:
positioning an electrode on a distal end of a lead within a pulmonary artery, such that the electrode is adjacent a baroreceptor site; and
delivering a baroreflex stimulation pulse train to a baroreceptor in the pulmonary artery via the electrode, the pulse train being delivered for about 5 seconds to about 10 seconds each minute at a voltage of about 0.1 volts to about 10 volts and a frequency of about 10 Hz to 150 Hz.

24. The method of claim 23, wherein positioning the electrode includes providing the distal end of the lead with a biased portion such that at least a portion of an outer diameter of the biased portion abuts a wall of the pulmonary artery.

25. The method of claim 24, wherein positioning includes positioning a biased portion having an outer diameter of about 10 to 20 mm.

26. The method of claim 24, wherein positioning includes positioning the biased portion to fix the electrode in place by frictional forces.

27. The method of claim 23, wherein positioning the electrode includes providing the distal end with a positive fixation mechanism to implant the electrode against a wall of the pulmonary artery.

28. The method of claim 23, wherein the electrode is adapted to be chronically implanted in the pulmonary artery.

29. The method of claim 23, further including monitoring a blood pressure to sense an efficacy of the baroreflex stimulation pulse train and to provide a signal indicative of the efficacy of the baroreflex stimulation pulse train.

30. The method of claim 23, wherein positioning includes positioning the electrode proximate the ligamentum arteriosum of the left pulmonary artery.

31. The method of claim 23, wherein positioning includes feeding the electrode through a right ventricle and a pulmonary valve into the pulmonary artery to position the electrode in the pulmonary artery.

32. The method of claim 23, wherein delivering a baroflex stimulation pulse train includes an at least 10 hertz pulse train via the electrode.

33. A method comprising:
 positioning an electrode on a distal end of a lead within a pulmonary artery, such that the electrode is adjacent a baroreceptor site; and
 delivering a baroreflex stimulation pulse train to a baroreceptor in the pulmonary artery via the electrode, wherein positioning the electrode includes chronically implanting the electrode proximate the ligamentum arteriosum of the left pulmonary artery, and wherein delivering the baroreflex stimulation pulse train includes delivering a baroreflex stimulation signal to the baroreceptor such that the stimulation signal causes a lowering of blood pressure, wherein the signal is delivered for about 5 seconds to about 10 seconds each minute at a voltage of about 0.1 volts to about 10 volts and a frequency of about 10 Hz to 150 Hz.

34. The method of claim 33, further including monitoring a blood pressure to sense an efficacy of the baroreflex stimulation pulse train and to provide a signal indicative of the efficacy of the baroreflex stimulation pulse train.

* * * * *